(12) United States Patent
Gianotti et al.

(10) Patent No.: US 9,327,101 B2
(45) Date of Patent: May 3, 2016

(54) LENGTH AND DIAMETER ADJUSTABLE BALLOON CATHETER

(71) Applicant: ABBOTT CARDIOVASCULAR SYSTEMS INC., Santa Clara, CA (US)

(72) Inventors: Marc Gianotti, Wiesendangen (CH); Jochen Bauer, Rielasingen (DE); Michael Jetter, Thayngen (CH)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 223 days.

(21) Appl. No.: 13/797,766

(22) Filed: Mar. 12, 2013

(65) Prior Publication Data

US 2013/0237950 A1 Sep. 12, 2013

Related U.S. Application Data

(63) Continuation of application No. PCT/US2011/052018, filed on Sep. 16, 2011.

(60) Provisional application No. 61/384,051, filed on Sep. 17, 2010.

(51) Int. Cl.
  *A61M 25/10* (2013.01)
  *A61F 2/958* (2013.01)
  *A61M 25/00* (2006.01)

(52) U.S. Cl.
  CPC ............ *A61M 25/1006* (2013.01); *A61F 2/958* (2013.01); *A61M 25/10* (2013.01);
  (Continued)

(58) Field of Classification Search
  CPC ............ A61M 25/10; A61M 25/1002; A61M 2025/1086; A61M 2025/105

USPC ............. 604/96.01, 103.08, 103.09; 606/108, 606/159, 192, 194

See application file for complete search history.

(56) References Cited

U.S. PATENT DOCUMENTS

| 4,748,982 | A | 6/1988 | Horzewski et al. |
| 4,782,834 | A | 11/1988 | Maguire et al. |

(Continued)

FOREIGN PATENT DOCUMENTS

| EP | 0275230 | 7/1988 |
| EP | 2 450 010 | 5/2012 |

(Continued)

OTHER PUBLICATIONS

U.S. Appl. No. 13/797,596, filed Mar. 12, 2013.

(Continued)

*Primary Examiner* — Gerald Landry, II
(74) *Attorney, Agent, or Firm* — Baker Botts L.L.P.

(57) ABSTRACT

Adjustable balloon catheter including an inner tubular member that has an inflation lumen defined therein. An expandable member is coupled to the distal end portion of the inner tubular member and has an inner chamber in fluid communication with the inflation lumen. The expandable member is transitionable between a deflated configuration and an inflated configuration. The expandable member defines has a non-cylindrical shape along at least a portion of a working length thereof when in the inflated configuration. An outer tubular member is movable relative to the inner tubular member, the outer tubular member includes a distal end. The outer tubular member is moveable between an extended position disposed over the expandable member and a retracted position proximal to the extended position. The outer tubular member is selectively positioned between the extended position and the retracted position to define an exposed length of the working length of the expandable member.

28 Claims, 21 Drawing Sheets

(52) U.S. Cl.
CPC .... *A61M25/1002* (2013.01); *A61M 2025/0063* (2013.01); *A61M 2025/105* (2013.01); *A61M 2025/1063* (2013.01); *A61M 2025/1068* (2013.01); *A61M 2025/1079* (2013.01); *A61M 2025/1081* (2013.01)

(56) References Cited

U.S. PATENT DOCUMENTS

| | | |
|---|---|---|
| 4,976,690 A | 12/1990 | Solar et al. |
| 5,102,402 A | 4/1992 | Dror et al. |
| 5,246,421 A | 9/1993 | Saab |
| 5,295,959 A | 3/1994 | Gurbel et al. |
| 5,300,085 A | 4/1994 | Yock et al. |
| 5,370,655 A | 12/1994 | Burns |
| 5,423,754 A | 6/1995 | Cornelius et al. |
| 5,454,795 A | 10/1995 | Samson |
| 5,496,346 A | 3/1996 | Horzewski et al. |
| 5,514,093 A | 5/1996 | Ellis et al. |
| 5,549,551 A | 8/1996 | Peacock et al. |
| 5,611,775 A | 3/1997 | Machold et al. |
| 5,626,600 A | 5/1997 | Horzewski et al. |
| 5,649,909 A | 7/1997 | Cornelius et al. |
| 5,676,654 A | 10/1997 | Ellis et al. |
| 5,702,373 A | 12/1997 | Samson |
| 5,735,816 A | 4/1998 | Lieber et al. |
| 5,961,536 A | 10/1999 | Mickley et al. |
| 6,129,705 A | 10/2000 | Grantz |
| 6,174,327 B1 | 1/2001 | Mertens et al. |
| 6,234,951 B1 * | 5/2001 | Hastings .................... 600/3 |
| 6,287,285 B1 | 9/2001 | Michal et al. |
| 6,352,501 B1 | 3/2002 | Urick |
| 6,406,457 B1 | 6/2002 | Wang et al. |
| 6,495,152 B2 | 12/2002 | Steinbuchel et al. |
| 6,500,148 B1 | 12/2002 | Pinchuk et al. |
| 6,506,180 B1 | 1/2003 | Lary |
| 6,541,116 B2 | 4/2003 | Michal et al. |
| 6,579,277 B1 | 6/2003 | Rabiner et al. |
| 6,669,980 B2 | 12/2003 | Hansen et al. |
| 6,695,863 B1 | 2/2004 | Ramzipoor et al. |
| 6,884,257 B1 | 4/2005 | Cox |
| 7,241,344 B2 | 7/2007 | Worsham et al. |
| 7,780,716 B2 | 8/2010 | Pappas et al. |
| 7,794,489 B2 | 9/2010 | Shumer et al. |
| 7,799,065 B2 | 9/2010 | Pappas et al. |
| 7,828,766 B2 | 11/2010 | Durcan et al. |
| 8,080,048 B2 | 12/2011 | Andreas et al. |
| 8,431,145 B2 | 4/2013 | Toner et al. |
| 2002/0009535 A1 | 1/2002 | Michal et al. |
| 2002/0082552 A1 | 6/2002 | Ding et al. |
| 2002/0183716 A1 | 12/2002 | Herweck et al. |
| 2004/0234748 A1 | 11/2004 | Stenzel |
| 2005/0182475 A1 | 8/2005 | Jen et al. |
| 2006/0195136 A1 | 8/2006 | Yokoyama et al. |
| 2007/0088255 A1 | 4/2007 | Toner et al. |
| 2007/0191864 A1 | 8/2007 | Shumer et al. |
| 2007/0244501 A1 * | 10/2007 | Horn .................. A61L 29/085 606/194 |
| 2009/0105686 A1 | 4/2009 | Snow et al. |
| 2009/0157043 A1 | 6/2009 | Leonard et al. |
| 2009/0254063 A1 | 10/2009 | von Oepen et al. |
| 2010/0030183 A1 | 2/2010 | Toner et al. |
| 2011/0028784 A1 * | 2/2011 | Patil .................. A61B 1/015 600/106 |
| 2011/0125132 A1 * | 5/2011 | Krolik ............. A61B 17/22032 604/509 |
| 2011/0143014 A1 | 6/2011 | Stankus et al. |
| 2011/0218494 A1 | 9/2011 | Gerrans et al. |
| 2012/0035588 A1 | 2/2012 | Schoenle et al. |
| 2012/0116490 A1 * | 5/2012 | Wesselmann .......... A61F 2/958 623/1.11 |
| 2012/0232640 A1 * | 9/2012 | Horvers ..................... 623/1.11 |
| 2012/0296313 A1 * | 11/2012 | Andreacchi ...... A61M 25/0668 604/509 |
| 2012/0316638 A1 * | 12/2012 | Grad ..................... A61F 2/966 623/1.12 |
| 2013/0253467 A1 | 9/2013 | Gianotti et al. |

FOREIGN PATENT DOCUMENTS

| | | |
|---|---|---|
| WO | WO 81/02109 | 8/1981 |
| WO | WO 96/40349 | 12/1996 |
| WO | WO 2007/095125 | 8/2007 |
| WO | WO 2009/005933 | 1/2009 |
| WO | WO 2012/037507 | 2/2012 |
| WO | WO 2012/037510 | 3/2012 |

OTHER PUBLICATIONS

International Search Report and Written Opinion for PCT/US2011/052018, dated Nov. 15, 2011.
International Search Report and Written Opinion for PCT/US2011/052014, dated Nov. 17, 2011.
International Search Report and Written Opinion for PCT/US2014/025366, dated Sep. 10, 2014.
U.S. Appl. No. 13/793,620, filed Mar. 11, 2013.
U.S. Appl. No. 14/208,033, filed Mar. 13, 2014.
International Search Report and Written Opinion for PCT/US2013/068310, dated Jul. 17, 2014.
International Search Report and Written Opinion for PCT/US2013/030341, dated Dec. 3, 2013.
U.S. Appl. No. 13/793,620, Nov. 25, 2015 Non-Final Office Action.
U.S. Appl. No. 13/797,596, Dec. 18, 2015 Non-Final Office Action.

* cited by examiner

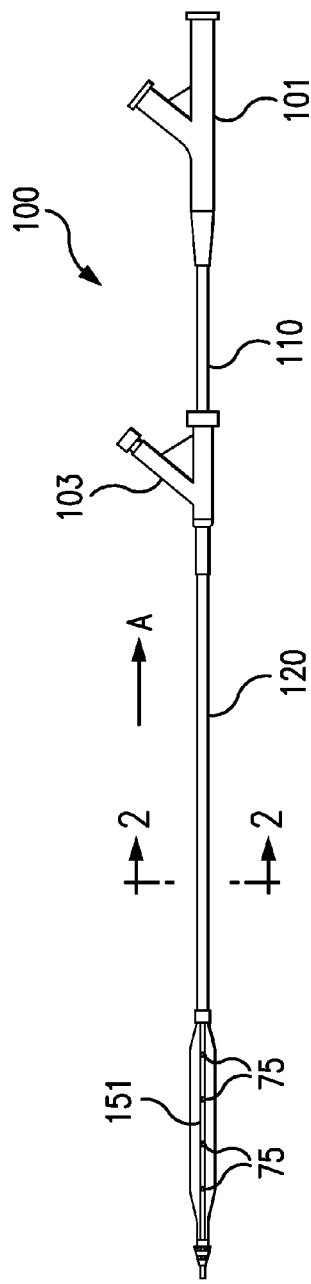
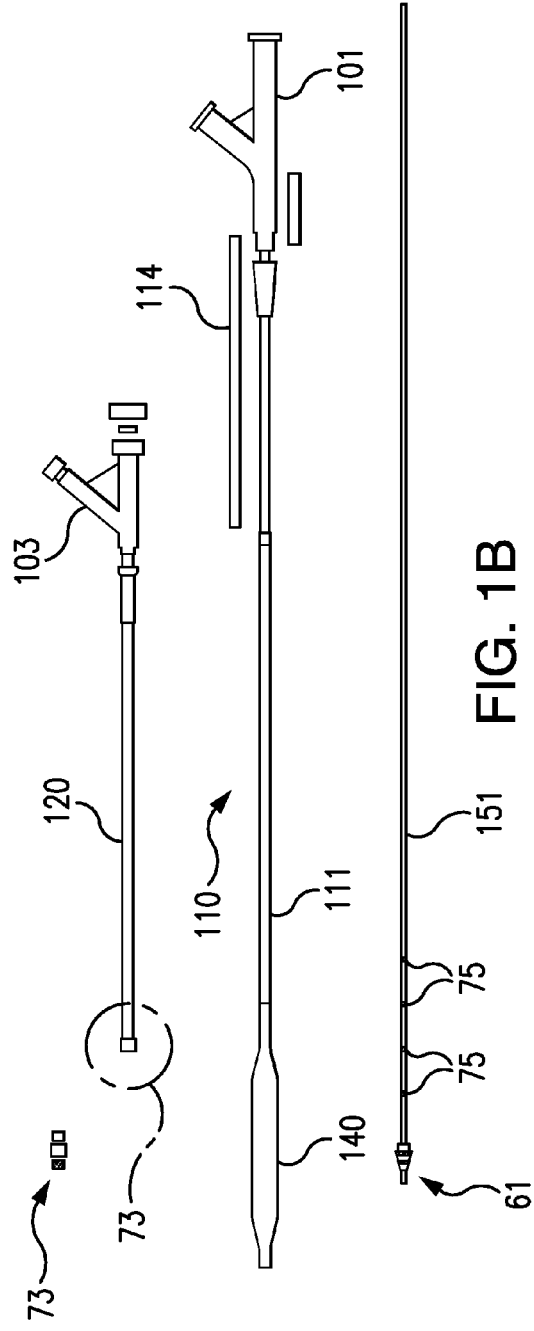

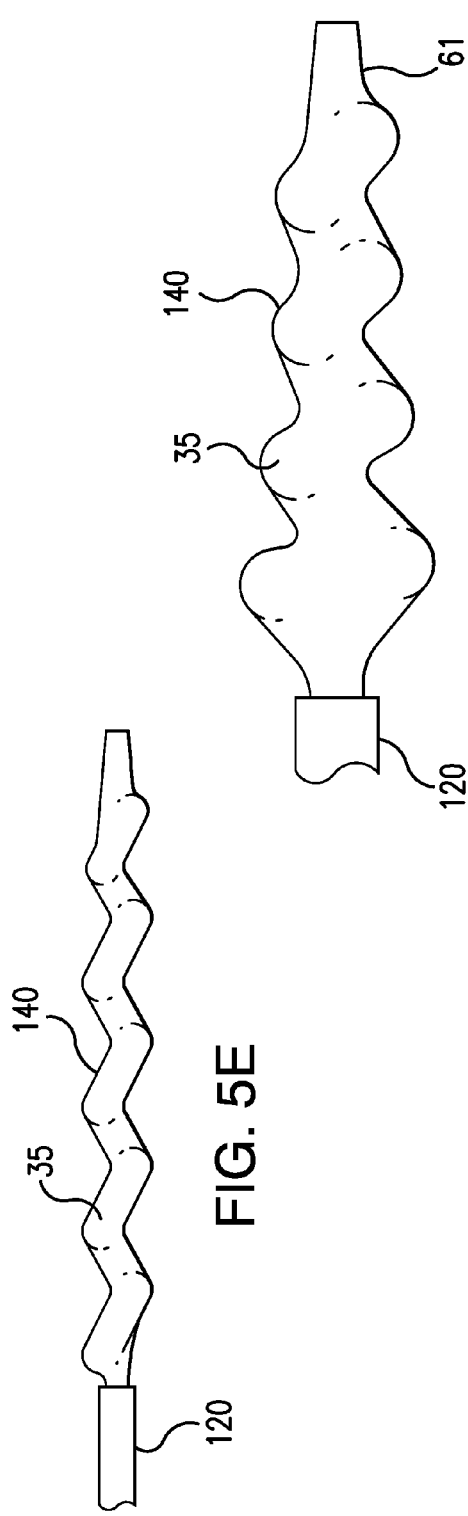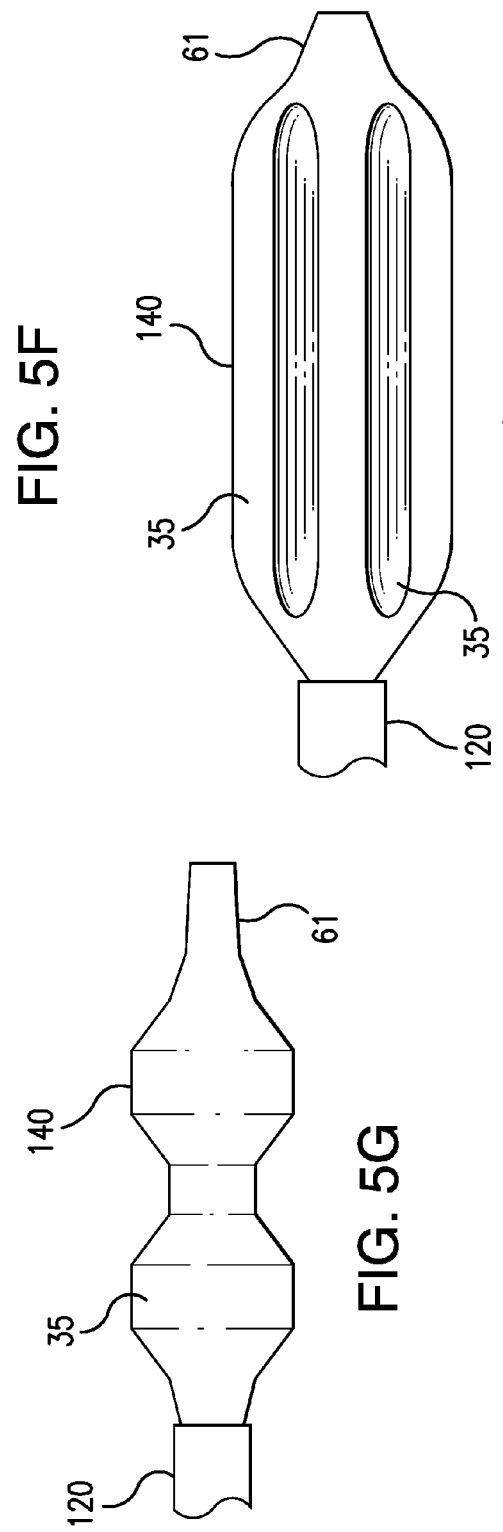

LENGTH AND DIAMETER ADJUSTABLE BALLOON CATHETER

CROSS-REFERENCE TO RELATED APPLICATION

This application is a continuation of International Application No. PCT/US2011/052018 filed, Sep. 16, 2011, which claims the benefit of U.S. Provisional Patent Application Ser. No. 61/384,051, filed Sep. 17, 2010, the contents of both of which are hereby incorporated by reference in their entireties herein.

BACKGROUND OF THE DISCLOSED SUBJECT MATTER

1. Field of the Disclosed Subject Matter

The disclosed subject matter relates to adjustable balloon catheters for treating the luminal systems of a patient. Specifically, the disclosed subject matter relates to catheters having an outer tubular member movable relative to the inner tubular member to define an exposed length of an expandable member.

2. Description of the Related Art

A variety of catheter devices are known in the art for treating the luminal system of a patient. Of such devices, many are directed to treating vascular systems, including both the cardiovascular system and the peripheral system of a patient. For example, the treatment of the cardiovascular system can include the performance of angioplasty or delivery of balloon-expandable or self-expanding interventional devices (e.g., stents, filters, coils). The treatment of the peripheral system includes treatment of the carotid, popliteal and renal vessels.

One such cardiovascular system treatment includes percutaneous transluminal coronary angioplasty (PTCA); a procedure for treating heart disease. This procedure generally entails introducing a catheter assembly into the cardiovascular system of a patient via the brachial or femoral artery, and advancing the catheter assembly through the coronary vasculature until a balloon portion thereon is positioned across an occlusive lesion. Once in position across the lesion, the balloon is inflated to a predetermined size to radially compress against the atherosclerotic plaque of the lesion to remodel the vessel wall. Subsequently, the balloon is deflated to allow the catheter assembly to be withdrawn from the vasculature.

With treatment of the peripheral system, conventional catheters are configured to treat a specific type of lesion, such as short, long, diffuse, or focal lesions. As such, it is necessary to select in advance the corresponding balloon catheter to treat the lesion of interest. However, conventional catheters are not configured to treat multiple lesions at a single time.

Furthermore, the site of the occlusive lesion can often only be reached by a tortuous pathway through the vasculature of the patient. The difficulty in accessing such regions requires that a successful catheter must be sufficiently flexible longitudinally to follow the tortuous path to the desired site, and at the same time, sufficiently stiff axially to allow the distal end of the catheter to be pushed or otherwise manipulated from an external access location.

To address this problem, catheters having varied flexibility along their length have been developed. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; and U.S. Pat. No. 5,649,909 to Cornelius discloses a catheter having a proximal portion with greater stiffness due to the application of a polymeric coating thereto.

Such conventional methods and systems generally have been considered satisfactory for their intended purpose. However, there remains a continued need in the art for an improved catheter having varied flexibility to enhance pushability, kink resistance and versatility.

In addition to PTA, PICA, and atherectomy procedures, commonly, adjustable balloon catheters are used to the peripheral system such as in the veins system or the like. For instance, an adjustable balloon catheter is initially advanced over a guidewire to position the balloon adjacent a stenotic lesion. Once in place, the balloon is then inflated, and the restriction of the vessel is opened. Typically, balloon catheters are structured such that they have a balloon fastened at least at one end to the exterior of a hollow catheter shaft. The hollow interior of the balloon is in a fluid flow relation with the hollow interior of the shaft. Fluid under pressure can thereby be supplied to the interior of the balloon through the shaft in order to expand the balloon against an obstruction. Unlike balloons used for cardiovascular indications, however, balloons for peripheral indications or treatments are generally much longer in length, for example, approximately 220 mm or more.

Catheter balloons typically are of a fixed length and diameter, necessitating the use of different sizes of balloons, for example, to treat vessels of varying diameter and lesions or occlusions of varying lengths.

In addition to the above-described uses of balloon catheters in PTA, PTCA, atherectomy and peripheral system procedures, other balloon catheters can be used to deliver therapeutic drugs or agents. For example, the drug can be coated on the exterior of the balloon. Unfortunately, when such delivery methods are used to deliver a controlled volume of medication to a desired tissue location, the therapeutic agent can be wiped off the surface of the balloon during delivery through the tortuous lumen system or otherwise lost to systemic circulation.

In light of the foregoing, there is a need for an improved balloon catheter having enhanced pushability and crossability, adjustability of the balloon catheter in vivo, and enhanced protectability of any drugs positioned on an expandable member of the balloon catheter. Embodiments of the disclosed subject matter provide solutions for these issues.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a balloon catheter. The adjustable balloon catheter includes an inner tubular member having a proximal end portion, a distal end portion, and a length therebetween, the inner tubular member further having an inflation lumen defined therein. An expandable member is coupled to the distal end portion of the inner tubular member and has an inner chamber in fluid communication with the inflation lumen. The expandable member is transitionable between a deflated configuration and an inflated configuration. The expandable member defines a longitudinal axis and has a non-cylindrical shape along at least a portion of a working length thereof when in the inflated configuration. An outer tubular member is movable relative to the inner tubular member, the outer tubular member includes a distal end. The outer tubular member is moveable between an extended position disposed over the expandable member and a retracted position proximal to the extended position. The outer tubular member is selectively positioned between the extended position and the retracted position to define an exposed length of the working length of the expandable member.

Further in accordance with another aspect of the disclosed subject matter, an adjustable balloon catheter is provided including an inner tubular member having a proximal end portion, a distal end portion, and a length therebetween, the inner tubular member further having an inflation lumen defined therein. An expandable member is coupled to the distal end portion of the inner tubular member and has an inner chamber in fluid communication with the inflation lumen. The expandable member is transitionable between a deflated configuration and an inflated configuration, the expandable member defining a longitudinal axis and having a working length in the inflated configuration. An outer tubular member is movable relative to the inner tubular member, the outer tubular member including a distal end. The outer tubular member is moveable between an extended position disposed over the expandable member and a retracted position proximal to the extended position. The outer tubular member is selectively positioned between the extended position and the retracted position to define an exposed length of the working length of the expandable member. The inner tubular member extends at least partially through the expandable member, the inner tubular member having a plurality of inflation ports defined therein along the working length for fluid communication between the inflation lumen and the inner chamber.

Further in accordance with another aspect of the disclosed subject matter, a method of deploying a medical is provided including providing an adjustable balloon catheter including the features as previously described. The method further includes retracting the outer tubular member in a proximal direction to define the exposed length of the working length of the expandable member, inflating the exposed length of the expandable member to the inflated configuration, and deflating the expandable member to the deflated configuration.

Further in accordance with another aspect of the disclosed subject matter, an adjustable balloon catheter is provided including an inner tubular member having a proximal end portion, a distal end portion, and a length therebetween, the inner tubular member further having an inflation lumen defined therein. An expandable member is coupled to the distal end portion of the inner tubular member and has an inner chamber in fluid communication with the inflation lumen. The expandable member is transitionable between a deflated configuration and an inflated configuration. The expandable member defines a longitudinal axis and a working length along at least a portion of the expandable member. An outer tubular member is provided having a distal end, the outer tubular member being moveable relative to the inner tubular member between an extended position disposed over the expandable member and a retracted position proximal to the extended position. The outer tubular member is selectively positioned to a selected position between the extended position and the retracted position to define an exposed length of the expandable member. The catheter has a stiffness profile and a flexibility profile along a length thereof. At least one of the stiffness profile and the flexibility profile is selectively adjustable by the selected position of the outer tubular member relative the inner tubular member.

Further in accordance with another aspect of the disclosed subject matter, a method of deploying a medical is provided including providing an adjustable balloon catheter including the features as previously described and moving the outer tubular member relative to the inner tubular member to adjust at least one of the stiffness profile and the flexibility profile of the catheter in a proximal direction.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

FIG. 1A is a side view of a representative balloon catheter in accordance with the disclosed subject matter.

FIG. 1B is an exploded view of the representative balloon catheter of FIG. 1A in accordance with the disclosed subject matter.

FIGS. 5A-5H are schematic side views of different embodiments of the expandable member, in accordance with embodiments of the disclosed subject matter.

DETAILED DESCRIPTION

Figure 2:
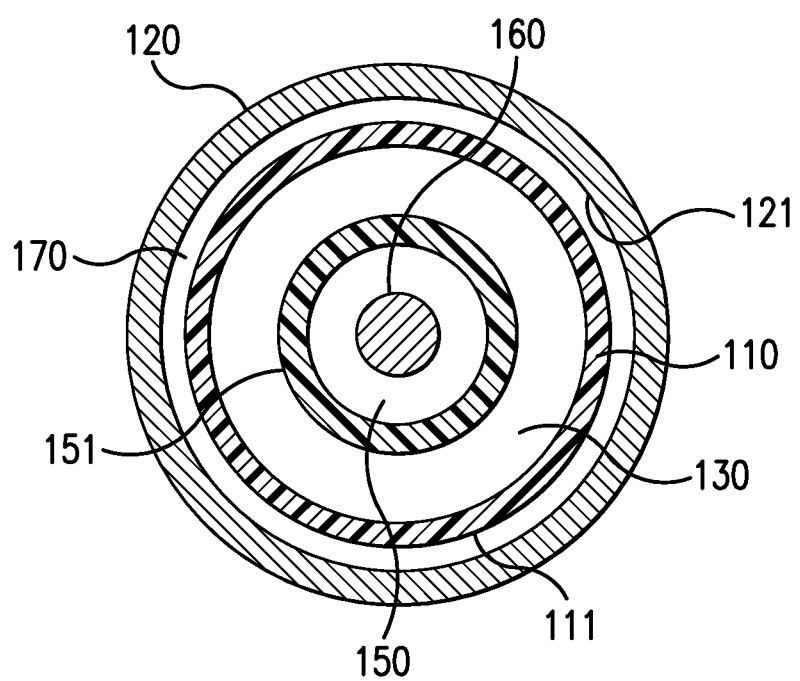
FIG. 2 is a cross sectional view of the catheter of FIG. 1A taken along line 2-2 which has a coaxial configuration, according to an embodiment of the disclosed subject matter.

Presently, catheter balloon materials can be classified as compliant, semi-compliant, or non-compliant balloons. Compliance can be defined as the increase in the balloon diameter above nominal balloon pressure. Generally, non-compliant balloons have less increase in diameter than semi-compliant balloons, which in turn have less increase in diameter than compliant balloons.

Compliant balloons expand and stretch with increasing pressure within the balloon, and are made from such materials as silicone, thermoplastic elastomers (TPEs), and polyethylene or polyolefin copolymers. Non-compliant balloons, made from such materials as polyethylene terephthalate (PET) or polyamides, remain substantially at a pre-selected diameter as the internal balloon pressure increases beyond that required to fully inflate the balloon. However, noncompliant balloons generally have relatively low flexibility and softness, so that it has been difficult to provide a low compliant balloon with high flexibility and softness for enhanced catheter trackability. A balance is typically struck between the competing considerations of softness/flexibility and noncompliance, which, as a result, has limited the degree to which the compliance of catheter balloons can be further lowered.

Compliant balloon materials provide a degree of softness to the balloon which aids its passage through, and expansion within, e.g., blood vessels. Known compliant balloon materials also can display good abrasion and puncture resistance at thicknesses typically used for medical device balloons.

Reference will now be made in detail to embodiments of the disclosed subject matter, an example of which is illustrated in the accompanying drawings. The disclosed subject matter will be described in conjunction with the detailed description of the system.

As disclosed herein, the devices presented herein can be used for treating the luminal system of a patient. The disclosed subject matter is particularly suited for treatment of the cardiovascular system and the peripheral system of a patient. The treatment of the cardiovascular system includes the performance of angioplasty or delivery of balloon-expandable or self-expanding interventional devices (e.g., stents, filters, coils). The treatment of the peripheral system includes, but is not limited to, treatment of the carotid, popliteal and renal vessels. Accordingly, the present disclosed subject matter is also suitable far a variety of particular endovascular vessels.

With treatment of the peripheral system, catheters according to embodiments of the disclosed subject matter can further be used in vessels with multiple lesions, such as, but not limited to, below the knee vessels. Thus, the adjustable balloon catheter according to an embodiment of the disclosed subject matter is not limited to a single long, short, diffuse, or focal lesion. The adjustable balloon catheter can treat any combination lesions due to the ability of the catheter to adapt to specific lesion or combination of lesions.

In accordance with one aspect of the disclosed subject matter, and adjustable balloon catheter is provided. The adjustable balloon catheter comprises an inner tubular member having a proximal end portion, a distal end portion, and a length therebetween. The adjustable balloon catheter further has an inflation lumen defined therein. An expandable member is coupled to the distal end portion of the inner tubular member and has an inner chamber in fluid communication with the inflation lumen. The expandable member is transitionable between a deflated configuration and an inflated configuration. The expandable member defines a longitudinal axis and has a non-cylindrical shape along at least a portion of a working length thereof when in the inflated configuration. The expandable member, or balloon as depicted herein, has an outer surface and an inner surface disposed at the distal end portion of the catheter shaft.

An outer tubular member is movable relative to the inner tubular member. The outer tubular member includes a distal end. The outer tubular member is moveable between an extended position disposed over the expandable member and a retracted position proximal to the extended position. The outer tubular member is selectively positioned between the extended position and the retracted position to define an exposed length of the working length of the expandable member.

Additionally or alternatively, the catheter has a stiffness profile and a flexibility profile along a length thereof. At least one of the stiffness profile and the flexibility profile is selectively adjustable by the selected position of the outer tubular member relative the inner tubular member For purpose of explanation and illustration, and not limitation, an embodiment of an adjustable balloon catheter, at least a portion of which is delivered within a vasculature, is shown schematically in FIG. 1A. FIG. 1B is an exploded view of FIG. 1A. Particularly and as illustrated, the adjustable balloon catheter 100 includes an inner tubular member (or catheter shaft) 110 having a proximal end portion, a distal end portion, and a length therebetween. The inner tubular member 110 can include a variety of suitable configurations. For example, but not limitation, in one embodiment the inner tubular member can comprise an over-the-wire (OTW) configuration. In this embodiment, the inner tubular member includes a guidewire lumen 150 extending generally across the entire length of the inner tubular member. A guidewire 160 can be introduced into the guidewire lumen 150, in a conventional manner as known.

Alternatively, the catheter can be configured with a rapid exchange configuration (RX). In this embodiment, a guidewire lumen 150 extends to a proximal guidewire port spaced distally from a proximal end portion of the inner tubular member. In either the OTW or the RX configuration, the inner tubular member can be provided with a co-axial arrangement or a multi-lumen arrangement. Further, the inner tubular member can be a single tube or an assembly of components coupled together. For purpose of example, and not limitation, the inner tubular member of the catheter embodied herein for peripheral vascular use includes a tapered L12 shaft with an outer diameter of approximately 1.08 mm, and a length of approximately 120 cm. Those skilled in the art will recognize that other configurations and known materials of construction can be used without departing from the scope of the disclosed subject matter.

For example, and as shown in FIG. 2, for the purpose of illustration and not limitation, a representative cross-sectional view of a co-axial arrangement is provided. The cross-sectional view is taken along lines 2-2 of FIG. 1A. In this manner, the inner tubular member can further include a guidewire tube 151 defining the guidewire lumen 150 therein, and an inflation lumen 130 defined annularly between the inner tubular member 110 and the guidewire tube 151. Further, the guidewire lumen can be formed by a thin membrane of suitable strength to prevent the guidewire from penetrating therethrough and minimize increases in cross-sectional profile of the inner tubular member. Alternatively, the guidewire tube 151 can be a multilayer construction, such as, but not limited to, a layer of Nylon-L25, a bonding layer such as Prim, and a layer of high-density polyethylene (HDPE).

Figure 3:
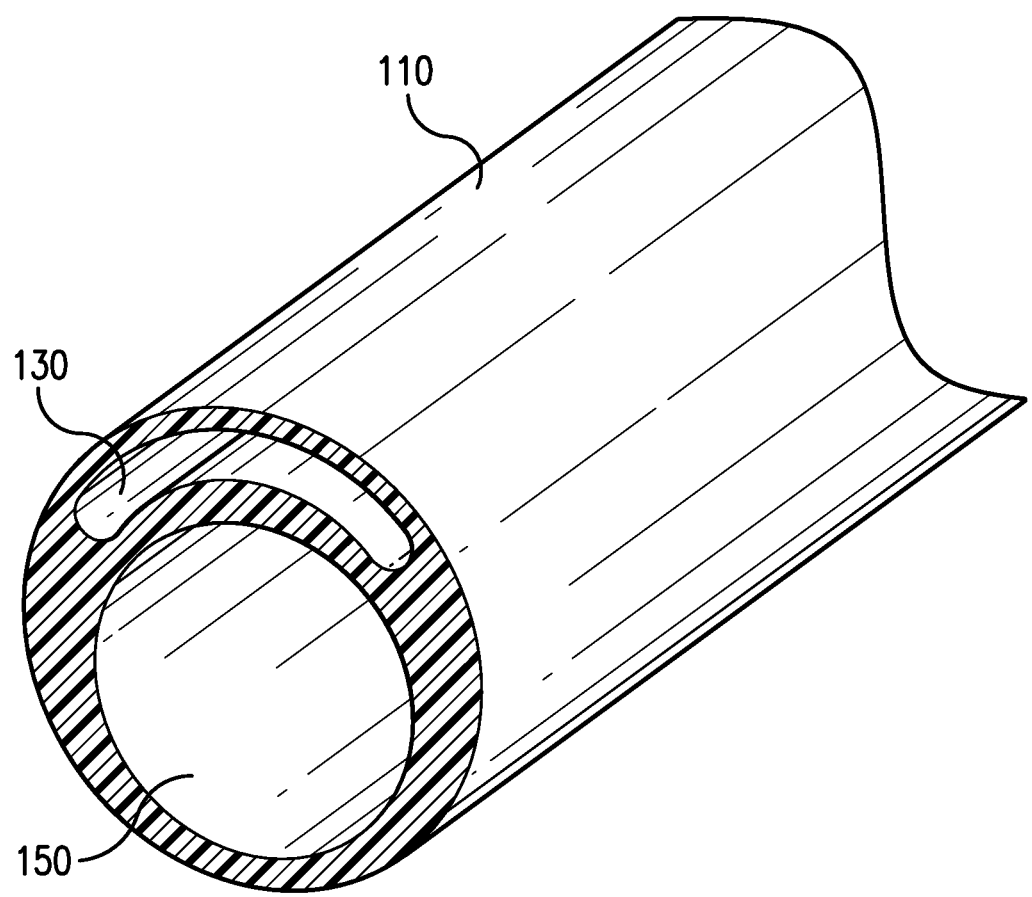
FIG. 3 is a cross-sectional view of an inner tubular member having a multilumen configuration, according to another embodiment of the disclosed subject matter.

In accordance with another embodiment, as depicted in FIG. 3, the inner tubular member can be a multi-lumen arrangement. For example, but not limitation, the inner tubular member 110 can be a monolithic member with the multi-lumen arrangement. In such embodiment, the inner tubular member 110 defines an inflation lumen 130 and a guidewire lumen 150, therein. The guidewire lumen 150 permits the catheter 100 to be delivered over a guidewire 151.

In either embodiment, the inner tubular member 110 comprises an exterior surface 111 and defines the inflation fluid lumen 130 therein. The inflation lumen is in fluid communication with the inner chamber of the expandable member 140, as described further below. The inflation lumen 130 defines a pathway for fluid to travel along the inner tubular member 110. Fluid can be introduced into the fluid lumen 130 at a proximal end of the catheter 100 via a luer adaptor or the like. The inflation lumen 130 can supply an inflation medium under positive pressure and can withdraw the inflation medium, e.g., by negative pressure, from the expandable member. The expandable member can thus be inflated and deflated, as further discussed below.

In an alternate embodiment, the inflation lumen and the guidewire lumen are combined and comprise a single shared lumen. For such co-axial arrangements, fluid can thus flow within the shared lumen with a guidewire 151 positioned therein. In such configuration, the inner tubular member 110 can comprise proximal and distal guidewire seals to sealingly engage the guidewire 151 disposed within the fluid lumen. The shared lumen can further have a stop, alone or in addition to the seals, at the distal end to allow the guidewire to proceed past the distal end of the catheter and to prevent the fluid from escaping the shared lumen. The seal or stop provides a recess to allow the guidewire to continue in the guidewire lumen. Such coaxial configurations allow for reduced diameter of the inner tubular member, and thus reduced profile.

As depicted in FIG. 1A, an adapter or manifold 101 can be provided at the proximal end of the catheter for access to the inflation lumen and is configured for connecting to a fluid source (not shown). The manifold can have a Y-shape with a luer connector at the proximal end of one branch to receive the fluid source, and a separate hemostatic valve on another branch to receive a guidewire. A conventional device, such as but not limited to an indeflator or a syringe, can be connected to the luer connector to introduce the fluid to the fluid lumen. A locking mechanism can further be provided to lock the operating position of the indeflator or syringe.

The indeflator or other fluid source can be configured to control the inflation and deflation of the expandable member. A pressure gauge can be provided with the indeflator to monitor and/or maintain the pressure system of the catheter. The indeflator likewise can allow for the rapid release of pressure. The indeflator can have a locking mechanism to maintain negative pressure in the catheter, which can decrease the profile of the catheter. The catheter is sized and configured for delivery within a body lumen, such as a vasculature, and particularly through a tortuous anatomy.

Figure 4:
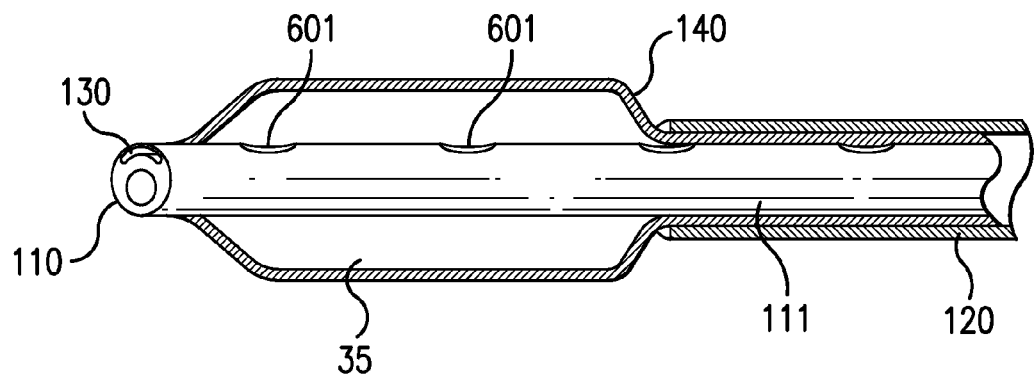
FIG. 4 is a schematic view of a catheter having a plurality of inflation ports, according to the disclosed subject matter.

As previously noted, an expandable member is coupled to the distal end portion of the inner tubular member. The expandable member 140, or balloon as depicted herein, has an exterior surface and an interior surface. The interior surface of the expandable member defines an inner chamber in fluid communication with the inflation lumen 130 of the inner tubular member. In accordance with one aspect, the inner tubular member can extend at least partially through the expandable member. For purpose of illustration and not limitation, FIG. 4 shows the inner tubular member extending the entire length of the expandable member. As embodied herein, the plurality of inflation ports 601 can be defined in the inner tubular member along the working length of the expandable member to ensure fluid communication with the inner chamber 35. The plurality of inflation ports provides enhanced inflation and deflation of the expandable member through compressed areas.

The expandable member 140 is transitionable between a deflated configuration and an inflated configuration. The outer tubular member 120, as described further below, is retracted in a proximal direction to define an exposed length of the expandable member. The expandable member has an overall length with a working length extending at least a portion of the overall length. The expandable member defines a longitudinal axis and can have a non-cylindrical shape along at least a portion of the working length thereof when in the inflated configuration. As embodied herein, for illustration and not limitation, at least a portion of the exterior surface of the expandable member along the working length is configured to engage a body lumen of a patient when the expandable member is in the inflated configuration.

In accordance with one aspect of the disclosed subject matter, a variety of different shapes can be used for the expandable member, wherein the shape of the expandable member can depend upon the desired application. As embodied herein, at least a portion of the working length of the expandable member has a non-cylindrical shape when in the inflated configuration. In one embodiment, the expandable member includes a cylindrical shape along a portion of the working length in the inflated configuration. In further embodiments, the shape can have further suitable shapes, such as non-cylindrical, as discussed herein.

Figure 5A:
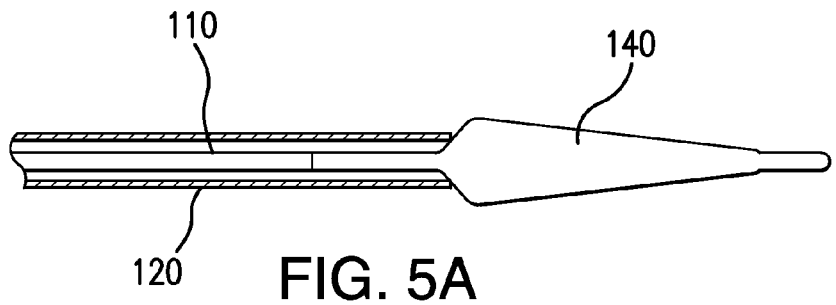
Figure 5B:
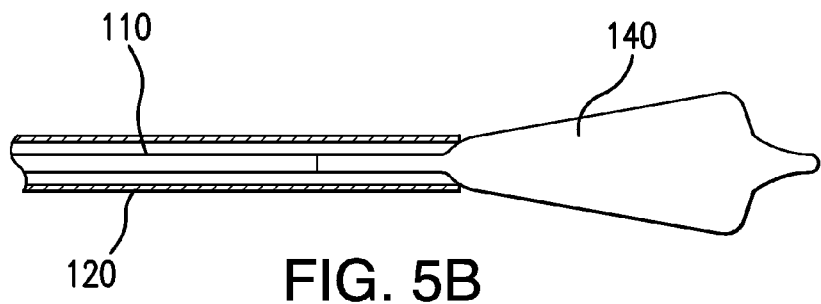

For purpose of explanation and illustration, and not limitation, FIGS. 5A-H are examples of various suitable shapes of the expandable member. For instance, FIG. 5A is a schematic view of the distal end of the disclosed catheter showing the exposed length of the expandable member in its inflated configuration with a frustoconical, generally conical, or tapered shape with the narrower end located at the distal end of the expandable member. The outer diameter of the expandable member of this embodiment increases toward the proximal end of the expandable member. Alternatively, FIG. 5B is schematic view of another embodiment of the distal end of the disclosed catheter showing the exposed length of the expandable member in its inflated configuration with a frustoconical, generally conical, or tapered shape where the narrower end is located at the proximal end of the expandable member, such that the outer diameter of the expandable member increases toward the distal end of the expandable member. In this manner, the overall diameter of the expandable member when inflated can be selected depending upon the exposed length of the expandable member.

That is, by retraction of the outer tubular member 120, as described further below, the outer diameter of the expandable member is adjustable based upon the selected exposed length of the expandable member. For the purpose of explanation and illustration, and not limitation, FIGS. 6A-D depict an embodiment of a conical expandable member in accordance with the disclosed subject matter. The outer diameter of the inflated expandable member at the proximal end is greater than and tapers continuously toward the outer diameter of the expandable member at the distal end of the balloon. For example, if the outer diameter is approximately 6 mm at the proximal end and decreases to about 2 mm at the distal end of the balloon, then the overall diameter would be about 4 mm at the proximal end if only half the working length is exposed. The overall diameter of the expandable member is thus selected as the maximum diameter of the exposed length.

Figure 6A:
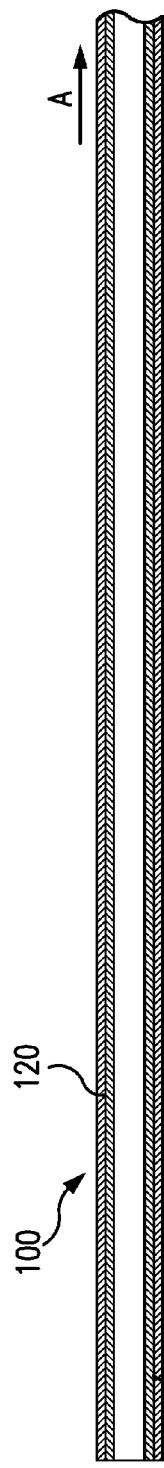
FIGS. 6A-6D are schematic images of a catheter in accordance with embodiments of the disclosed subject matter with the retractable outer tubular member selectively positioned to expose various lengths and corresponding diameters of the expandable member.
Figure 6B:
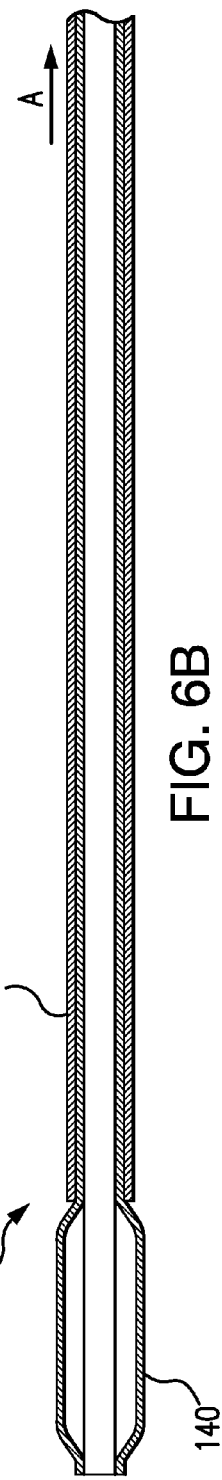
Figure 6C:
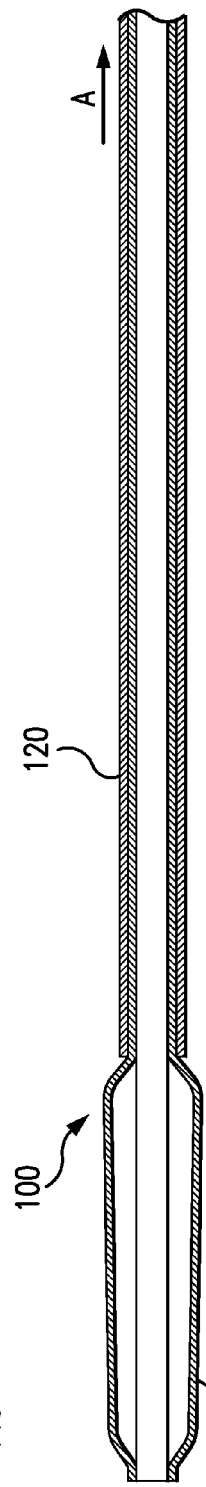
Figure 6D:
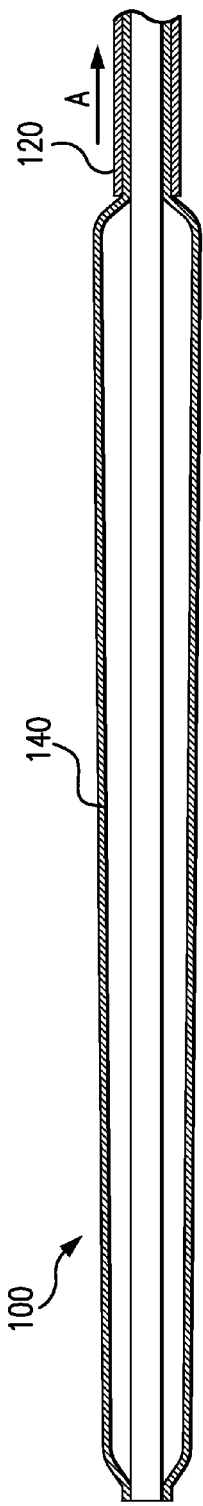

FIG. 6A shows the outer tubular member 120 completely extended in the extended position. FIGS. 6B and 6C show the outer tubular member selectively positioned in retracted positions to expose various lengths and diameters of the expandable member. In this embodiment, as the outer tubular member is retracted, the expandable member increases in diameter in the inflated configuration due to the conical configuration of the expandable member. FIG. 6D shows the outer tubular member further retracted. The length of the expandable member can vary depending upon the desired application and intended use. The length and diameter of the expandable member can thus be adjusted by selectively retracting the outer tubular member. Those skilled in the art will recognize that the expandable member can be formed in various different shapes and sizes which are not shown without departing from the scope of the disclosed subject matter.

Figure 5C:
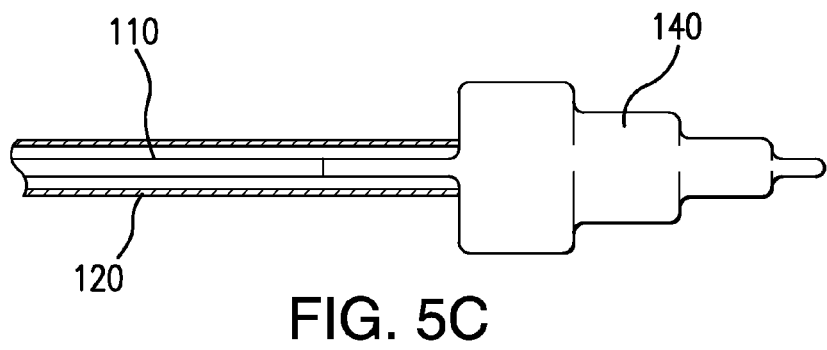
Figure 5D:
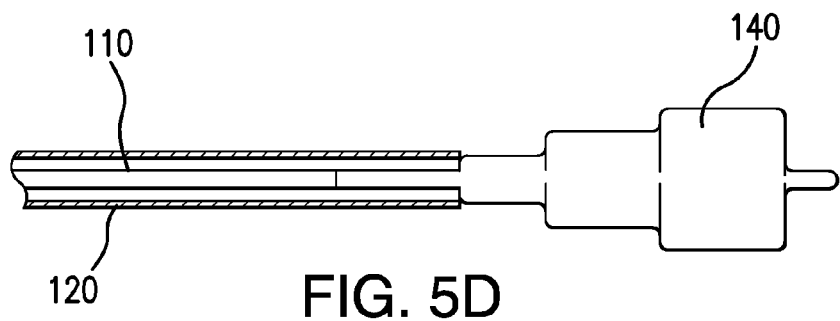

In a further embodiment, the non-cylindrical shape of the expandable member includes a distal end section having a first diameter and a proximal end section having a second diameter when in the inflated configuration. The first diameter can be different than the second diameter. For example, but not limitation, the non-cylindrical shape of the expandable member can have a stepped configuration. FIGS. 5C and 5D are schematic views of two embodiments of a stepped configuration with the expandable member in the inflated configuration. The outer diameter of the expandable member of FIG. 5C decreases with distance toward the distal end of the expandable member. The outer diameter of the expandable member of FIG. 5D increases with distance toward the distal end of the expandable member. Although only three steps are depicted in each of FIGS. 5C and 5D, any number of steps can be provided as desired as needed.

As provided in FIG. 5E, the expandable member can be a helical shape along the longitudinal axis in the inflated configuration. The helical shape extends radially from the longitudinal axis at a substantially constant distance along the working length in the inflated configuration. Accordingly, the exterior surface of the helical shaped expandable member remains at a substantially constant distance from the longitudinal axis. The exterior surface of the expandable member in the inflated configuration thus can define a helical flow path along the longitudinal axis. As with the spiral shape, the helical flow path prevents occlusions and fluid flow can continue across the catheter defined between the exterior surface of the expandable member and the wall of the body.

FIG. 5F is a schematic view of an expandable member including a spiral shape along the longitudinal axis in the inflated configuration. The spiral shape extends radially from the longitudinal axis at a varied distance along the working length in the inflated configuration. Accordingly, an exterior surface of the spiral shaped expandable member can vary in distance from the longitudinal axis. Further, the exterior surface of the expandable member in the inflated configuration thus can define a spiral flow path along the longitudinal axis. The spiral flow path prevents occlusion of the body lumen of a patient when the expandable member is in the inflated configuration. The spiral flow path thus allows fluid flow to continue across the catheter via the spiral flow path defined between the exterior surface of the expandable member and the wall of the body lumen of a patient.

According to another embodiment of the disclosed subject matter, an exterior surface of the expandable member can define at least one isolated chamber along the longitudinal axis in the inflated configuration, as depicted in FIG. 5G. In this embodiment, the expandable member includes different diameters along the length of the expandable member. For example, and not limitation, the expandable member can have at least two segments of the working length, each having a maximum outer diameter of at least the diameter of the body lumen of the patient at the site of treatment. Between the at least two segments, the expandable member has a further segment of the exposed length of the working length between the two segments and having an outer diameter when in the inflated condition less than the maximum outer diameter of either of the two segments to define the at least isolated one chamber. The expandable member can further include a plurality of isolated chambers spaced apart along the working length. The segments can have a variety of shapes, including spherical, frustroconical, or cylindrical. In embodiments having a plurality of cylindrical shapes, each adjacent cylindrical shape can have a different diameter to further define isolated chambers between adjacent cylindrical shapes.

As depicted in FIG. 5H, The exterior surface of the expandable member can be configured to define one or more longitudinal flow paths 55 along the longitudinal axis. For example, and as embodied herein for illustration and not limitation, the expandable member can include a variety of non-circular cross-sections such as square, U-shape or petal shaped along its longitudinal axis in the inflated configuration. The longitudinal flow path allows blood to continue distally past the catheter defined between the exterior surface of the expandable member and the walls of the body lumen of a patient.

In accordance with another aspect of the disclosed subject matter, the expandable member can be configured relative the outer tubular member so as to be completely exposed the entire length of the expandable member. In this manner, the proximal end of the expandable member will not be exposed when the outer tubular member is fully retracted as described further below, so as to allow the outer tubular member to be moved or returned distally relative to the inner tubular member. Thus, a folded balloon configuration can be used for the expandable member. For example, when the outer tubular member is in the extended configuration and positioned over the expandable member, the expandable member is in a folded arrangement within the outer tubular member. As the outer tubular member is retracted and the expandable member is inflated, the working length of the expandable member is no longer folded. However, a proximal portion of the expandable member will remain within the outer tubular member with the proximal portion folded within the outer tubular member. The folded proximal portion of the expandable member thus facilitates refolding of the expandable member after the expandable member is deflated and the outer tubular member is moved distally.

For purpose of example, the catheter and method as disclosed herein for refolding can be used for relatively long balloon lengths, such as peripheral balloons. In one embodiment, for purpose of example, the expandable member is a long balloon and has a length of approximately 220 mm. The approximate maximum working length of the expandable member can be approximately 200 mm, whereas the approximate folded proximal portion of the expandable member can be approximately 20 mm. Likewise, the refolding technique can be used with an expandable member having a short length, such as approximately 120 mm. In this embodiment, the maximum working length of the expandable member can be approximately 100 mm and the approximate folded proximal portion remaining in the outer tubular member can be approximately 20 mm.

To prevent the outer tubular member from being retracted beyond the desired working length, a stop mechanism can be employed. For example, but not limitation, the distal end of the catheter luer or other member configured to abut the proximal end of the outer tubular member prevent further movement of the outer tubular member with the proximal end of the expandable member still partially covered by the distal end of the outer tubular member.

In a further embodiment, the proximal end portion of the expandable member can include a reinforced proximal sleeve. The reinforced proximal sleeve can assist in resisting puncture of the expandable member, such as if the expandable member is to be inflated and deflated a number of times. The reinforced proximal sleeve can further protect the expandable member from the outer tubular member including any reinforcement of the outer tubular member if provided. The distal edge of the reinforced proximal sleeve can include a radiopaque material or have a suitable density to allow far radiopacity. The reinforced proximal sleeve also can prevent trumpeting effects of the outer tubular member and can reduce the kink stress along the expandable member. The reinforced proximal sleeve can also allow for refolding of the folded arrangement of the expandable member within the outer tubular member.

In accordance with another aspect of the disclosed subject matter, a therapeutic agent can be disposed on the expandable member. In this manner, the outer tubular member can protect the therapeutic agent during delivery of the catheter to the selected site. Additionally, the amount and location of drug released will be a function of the exposed length of the expandable member. The therapeutic agent can be for the treatment of a disease. Examples of suitable therapeutic agents include anti-proliferative, anti-inflammatory, antineoplastic, antiplatelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

In one embodiment, however, the therapeutic agents include a cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel. Other drugs include dexamethasone, statins, sirolimus, and tacrolimus.

In addition to the therapeutic agent, any of a variety of fluid compositions can be applied to the expandable member. The fluid can include compounds or additives, such as polymers, binding agents, plasticizers, solvents, surfactants, additives, chelators, fillers, excipients, and the like, or combinations thereof. Suitable excipients, binding agents and other components include those described in detail in U.S. patent application Ser. No. 12/636,079, which is hereby incorporated by reference in its entirety. In one embodiment, excipients include poly(ethylene glycol) (PEG), polyvinylpyrrolidone (PVP), polyoxyethylene sorbitan monooleate (tweens), poloxamer triblock copolymers of poly(ethylene oxide)-poly (propylene oxide)-poly(ethylene oxide) (Pluronics), carboxymethyl cellulose (CMC), and PEG phospholipids such as 1,2-distearolyl-sn-glycero-3-phosphoethanolamine-N-(methoxy(polyethylene glycol)-2000) (PEG-PE). In one embodiment, plasticizers include PEG, propylene glycol, N-methylpyrrolidone (NMP), glycerin, and tweens. Examples of possible compounds include zotarolimus, PVP and glycerol. In one embodiment the therapeutic agent can be provided in liquid form or dissolved in a suitable solvent. In another embodiment, the therapeutic agent is provided as a particulate and mixed in a suitable carrier for application as a fluid.

The fluid compositions, such as the therapeutic agents, can be applied to the expandable member using a variety of know techniques, such as spraying (air-atomization, ultrasonic, electrostatic, piezoelectric, etc.), spray drying, pneumatic spray, spray with patterning, electrospinning, direct fluid application, dip-coating, spin-coating, pipette coating, syringe coating, vapor deposition, roll coating, micro-droplet coating, ultrasonic atomization, or other means as known to those skilled in the art. The coating can be applied over at least a length or the entirety of the expandable member. By way of example, and not limitation, certain coating processes that can be used with the instant disclosed subject matter are described in U.S. Pat. No. 6,669,980 to Hansen; U.S. Pat. No. 7,241,344 to Worsham; U.S. Publication No. 2004/0234748 to Stenzel; and U.S. Patent Application Ser. No. 61/345,575, the entire disclosures of which are hereby incorporated by reference. In accordance with one embodiment of the disclosed subject matter, the coating can be applied to either a folded or inflated balloon. Furthermore, the coating can be directly applied into the folds of the folded balloons. The coating characteristics are affected by process variables. For example, for dip-coating process, coating quality and thickness can vary as an effect of variables such as number, rate, and depth of dips along with drying time and temperature.

In accordance with another aspect of the disclosed subject matter, the expandable member can include microcapsules on its outer surface. In this regard, the microcapsules are configured to encompass the coating and/or therapeutic agent. Upon inflation of the expandable member the microcapsules located on the surface of the expandable member contact the tissue of the arterial wall. Alternatively, the microcapsules can be formed in the wall of the expandable member surface or on the tissue engaging member. The coating and/or therapeutic agent can be released from the microcapsules by fracturing of the microcapsules and/or diffusion from the microcapsule into the arterial wall. The microcapsules can be fabricated in accordance with the methods disclosed in U.S. Pat. No. 5,102,402 to Dror or U.S. Pat. No. 6,129,705 to Grantz and the patents referenced therein, each of which is incorporated herein by reference in its entirety.

As previously disclosed, the catheter further includes an outer tubular member or sheath. For example, and as embodied for illustration and not limitation, FIGS. 1A and 1B and FIG. 2 illustrate the outer tubular member 120 has a proximal end, a distal end, a length, and an interior surface 121. The inner tubular member 110 is positioned within the outer tubular member 120 at the distal end of the catheter 100, such that the interior surface 121 of the outer tubular member 120 is directed toward the exterior surface 111 of the inner tubular member 110. The outer tubular member 120 is movable relative to the inner tubular member 110 along a length of the inner tubular member 110. For example, the outer tubular member 120 can be retracted in a direction A toward the proximal end of the catheter or extended distally. The outer tubular member 120 can be disposed at a distal end portion of the catheter or can extend the entire length of the catheter. The outer tubular member has a length at least equal to the length of the expandable member 140.

The outer tubular member 120 is movable relative the inner tubular member 110 between an extended position disposed over the expandable member 140 and a retracted position proximal to the extended position. The working length of the expandable member represents the maximum length that can be exposed outside the outer tubular member. The outer tubular member is selectively positioned between the extended position and the retracted position to define an exposed length of the working length of the expandable member, as further discussed herein. Additionally, the outer tubular member is selectively positioned to selectively adjust the stiffness profile and/or the flexibility profile along the length of the catheter as further described herein.

Figure 7A:
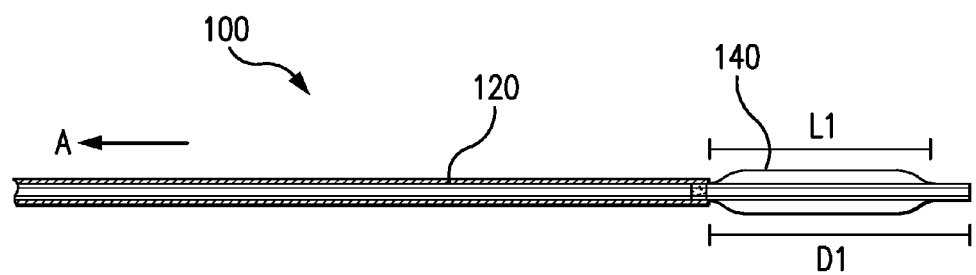
FIGS. 7A-7C are images of catheters in accordance with the disclosed subject matter with the retractable outer tubular member selectively positioned to expose various lengths of the expandable member, in accordance with an embodiment of the disclosed subject matter.
Figure 7B:
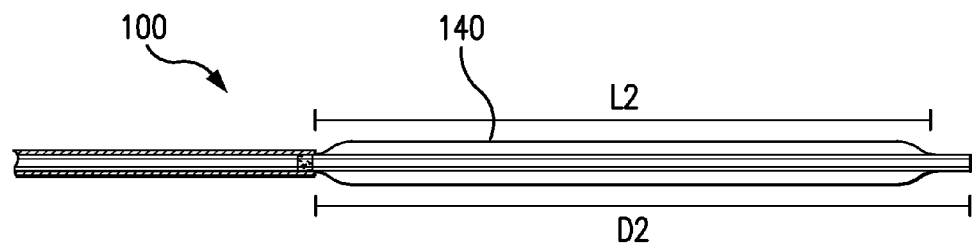
Figure 7C:
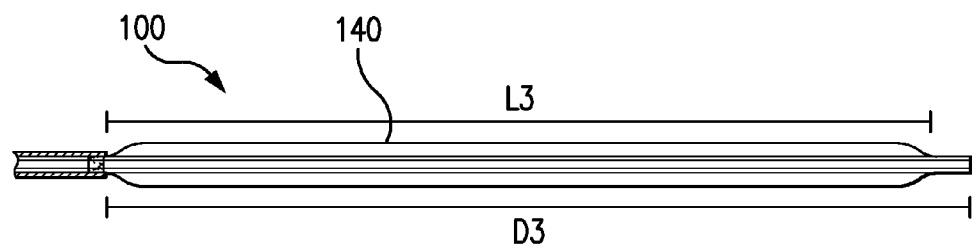

For purpose of explanation and illustration, and not limitation, FIGS. 7A-7C depict schematics of a representative catheter in accordance with the disclosed subject matter. The adjustable outer tubular member 120 is selectively positioned to expose various lengths of the expandable member. FIG. 7A depicts the adjustable outer tubular member 120 retracted a first distance D1 in the proximal direction A to expose a first exposed length L1 of the working length of the expandable member. FIG. 7B depicts the adjustable outer tubular member 120 retracted a second distance D2 to expose a second exposed length L1 of the working length of the expandable member. FIG. 7C depicts the adjustable outer tubular member 120 retracted a third distance D3 to expose a third exposed length L3 of the working length of the expandable member. The further the outer tubular member is retracted, the greater portion of the length of the balloon can be exposed.

A variety of actuators can be used to move the outer tubular member between the retracted position and the extended position. For example, the proximal end of the outer tubular member can be moved or otherwise actuated by a push-pull handle assembly. The outer tubular member can also be extended and retracted through the use of actuators as disclosed in U.S. Pat. Nos. 7,780,716 and 7,799,065, and U.S. patent application Publications 2005/0182475 and 2007/0191864, the contents of which are incorporated herein in their entirety.

The outer tubular member can be provided with a generally constant cross-section or diameter. Alternatively, the outer tubular member can define a first external diameter at its proximal end, and a second, different external diameter at its distal end. The first diameter can be smaller than the second diameter, or vice versa. For example, and in accordance with an embodiment of the disclosed subject matter, the outer tubular member can have a first diameter of about 4 French and a second diameter of about 5 French, although these dimensions can vary depending on the desired application.

In accordance with this aspect of the disclosed subject matter, a step can be provided to allow for the change in diameter between the proximal end and distal end of the outer tubular member 120. The step allows for the change in diameter to occur over a longer or shorter distance along the outer tubular member, depending on the application. Alternatively, a more gradual taper can be provided if desired.

The outer tubular member 120 protects the expandable member 140, and any coating or therapeutic agent on the expandable member, if provided, during delivery of the expandable member through a body lumen of a patient to the target site. In one aspect of the disclosed subject matter, the outer tubular member can prevent the release of drug from the surface of the expandable member prior to deployment at the desired site such that drug loss is minimized. The outer tubular member can be utilized to protect the coating of therapeutic agent from releasing from the expandable member during the movement of the adjustable balloon catheter through the body lumen. Furthermore, the outer tubular member can also protect the coating during shipping and storage before use.

In another embodiment of the disclosed subject matter, the inner surface of the outer tubular member is further formed having a non-uniform surface, such as a repeating pattern formed therein, the pattern forming a sinusoidal pattern about the circumference of the tubular member. By forming the surface in the manner described, frictional forces between the inner surface of the outer tubular member and the outer surface of the expandable member can be reduced by forming points of contact between the two surfaces instead of a continuous surface contact between the two surfaces. The multiple contact points reduce friction between the outer tubular member and the expandable member thereby requiring less force to retract the outer tubular member during use. The outer tubular member can be fabricated as a unitary member or fabricated of more than one element.

The outer tubular member can be constructed of a single layer of suitable material. For example, a suitable material can include, but is not limited to, polymer materials such as nylon, urethane, polyurethane, PEEK, PTFE, PVDF, Kynar, PE, HDPE, a trilayer material including L25, Plexar, or polyethylene of various suitable densities. The thickness of the single layer can vary in thickness along the length of the adjustable length catheter. Alternatively, the thickness of the single layer can remain substantially constant.

In accordance with another aspect of the disclosed subject matter, the outer tubular member can comprise a multilayer member and include, for example, an outer layer and an inner layer. The inner layer can be attached to or formed with the outer layer. For example, the multiple layers can be formed in a number of suitable manners including, but not limited to, separately and adhered or bonded together or co-extruded as a single member. The inner layer or liner can include a lubricious material to facilitate the sliding of the outer tubular member in a proximal direction when the outer tubular member is retracted. For example, different types of polymers such as PTFE or high-density polyethylene (HDPE) can be used for the inner layer. Additionally, other suitable lubricious polymers can be used. If desired, the inner layer of the outer tubular member can be formed with a varied wall thickness. For example, the wall thickness can be greater at the distal end than at the proximal end. The outer layer, alone or in combination with the inner layer, can provide sufficient strength to capture a medical device therein, as well as allow movement between extended position and the retracted position. Furthermore, the outer tubular member has sufficient axial strength or stiffness to enhance pushability of the catheter as desired and described further below.

In further accordance with the disclosed subject matter, the outer tubular member can include a reinforcing layer, such as braided material, disposed between the outer layer and the inner layer. For example, the reinforcing layer can be provided in the form of braided stainless steel filaments having rectangular or otherwise flattened cross-sections. Other woven or braided material likewise can be used, such as carbon fibers encased in a polymeric matrix. Likewise, reinforcing fibers can additionally or alternatively be incorporated between or into the inner layer and/or outer layer during the manufacturing process. The reinforcing layer need not be present through the entire length of the outer tubular member. Indeed, and in accordance with another aspect of the disclosed subject matter, the reinforcing layer can be provided or varied along selected portions of the outer tubular member or the inner tubular member to alter the flexibility and/or stiffness profiles therefrom. For example, the reinforcing layer can provided along the proximal portion the outer tubular member only. In one embodiment for purposes of illustration and not limitation, the outer tubular member can include an inner layer of PTFE with an inner diameter of 1.14 mm, a braided reinforcing layer of 0.0254 mm×0.0762 mm of 304V stainless steel wire at 25 PIC, and an outer layer of nylon with an inner diameter of 1.265 mm.

In accordance with an embodiment of the disclosed subject matter, the outer tubular member can have a wall thickness of about 6.0 mil, wherein inner layer and reinforcing layer have a thickness of about 2.0 mil, and outer layer has a thickness of about 4.0 mil. Wherein the dimensions above are provided as examples and should not be considered limiting in any manner.

When the outer tubular member is provided with an inner layer, outer layer and a reinforcing layer the outer tubular member can be formed in the following manner. First, the inner layer is formed through a tubular extrusion process, and disposed about a forming mandrel (not shown). The forming mandrel can have a shape that corresponds to the desired shape of the inside of the outer tubular member. The reinforcing layer can be provided in the form of a stainless steel braid material and is positioned over a predetermined length of inner layer, e.g. a distal portion of the inner layer can remain uncovered by the reinforcing material. The outer layer is then extruded over the reinforcing layer. The outer layer can be provided in the form of two separate tubular members that are overlapped slightly at their ends over reinforcing layer. Each portion of outer layer can be a different material selected to provide a different durometer as desired. The two portions of outer layer can overlap by an amount, such as, but not limited to, about 2.0-2.5 MM. Next, a sleeve of heat shrinkable material is positioned over the entire outer tubular member assembly. When heat is applied to the assembly, the heat shrinkable tubing shrinks and causes inner layer to fuse with outer layer, trapping reinforcing layer therebetween. The heating process also causes inner layer to conform to the shape of the forming mandrel. Thus, if it is desired to have an outer tubular member with a varied and/or stepped diameter as described above, the mandrel can be formed accordingly. After the assembly cools, the heat shrinkable tubing is cut away, leaving behind the outer tubular member 120.

Figure 8:
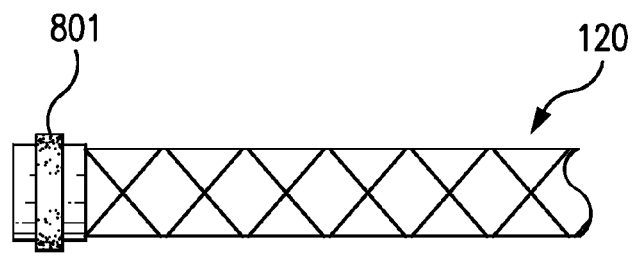
FIG. 8 is an embodiment of the outer tubular member with a braided polymer shaft, in accordance with an embodiment of the disclosed subject matter.

In accordance with another aspect of the disclosed subject matter referring to FIG. 8, for purpose of illustration and not limitation, an alternative embodiment of an outer tubular member 120 is shown. At least a portion of the outer tubular member, e.g. the distal end portion, as shown, is formed of a brained polymer sleeve with a marker 801 at its distal end. The braided polymer sleeve increases flexibility and softness of the outer tubular member. Additionally, to improve flexibility, the spiral plastics can be used in the construction of the outer tubular member. The marker can be a radiopaque metallic ring or other member suitable for the intended use. Alternatively, the marker can be constructed using tungsten loaded polymer plastics for increased softness. Other suitable known markers can be used, as further discussed herein.

Figure 9:
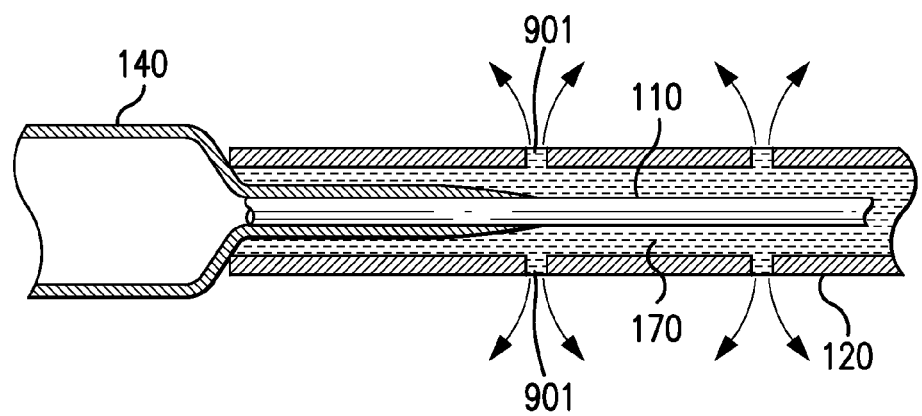
FIG. 9 is a schematic view of the outer tubular member having flushing ports, in accordance with an embodiment of the disclosed subject matter.

In a further embodiment of the disclosed subject matter, a flushing lumen 170 is defined between the inner tubular member and the outer tubular member, as depicted in FIG. 9. In accordance with another aspect, the outer tubular member includes at least one flushing port 901 defined therethrough in fluid communication with the flushing lumen, as depicted in FIG. 9. A fluid, such as but not limited to, a contrast media or therapeutic agent, can be introduced into the flushing lumen by an adapter in communication therewith. The contrast media or agent can exit the flushing lumen 170 via the at least one flushing port 901.

In accordance with another aspect of the disclosed subject matter, the catheter has a stiffness profile and a flexibility profile wherein at least one of the stiffness and the flexibility is selectively adjustable by the selected position of the outer tubular member relative the inner tubular member. For example, and as embodied herein, the stiffness and/or flexibility profile of the catheter can be a function of a stiffness and/or flexibility profiles, respectively, of the components of the adjustable balloon catheter. That is, the inner tubular member can have a stiffness profile along the length thereof. A plurality of factors can effect the stiffness of the inner tubular member including, but not limited to, the materials of construction of the inner tubular member, the thickness of the inner tubular member, the application of radiopaque markers, the application of an inner tubular member tip, the length of an expandable member coupled thereto, and other applicable factors as further described. Similarly, the plurality of factors together define the stiffness and/or flexibility profile of the inner tubular member.

Figure 10A:
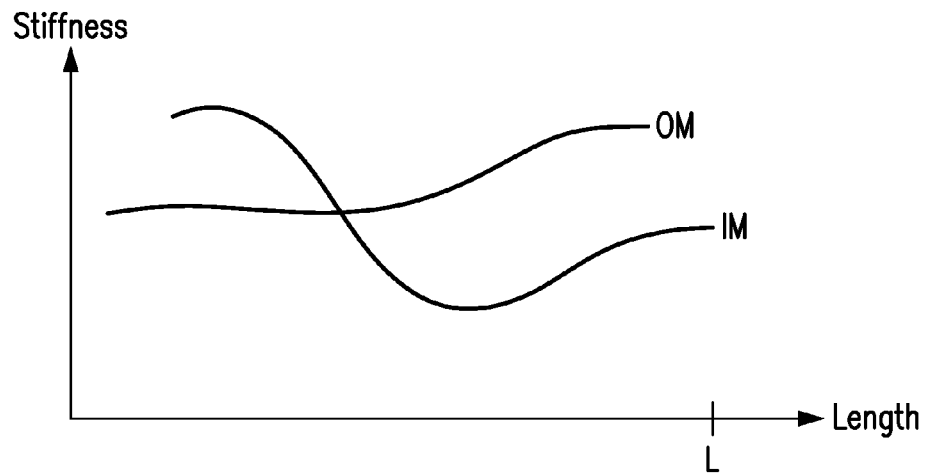
FIG. 10A shows a distal end section of a catheter with the outer tubular member in the extended position, in accordance with an embodiment of the disclosed subject matter.
Figure 10B:
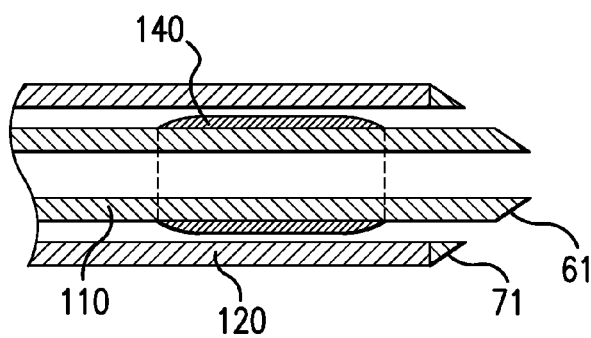
FIG. 10B shows a representative length-stiffness graph of the inner tubular member and the outer tubular member respectively, of the catheter of FIG. 10A in accordance with an embodiment of the disclosed subject matter.

As desired, and in accordance with another aspect herein, the inner tubular member and the outer tubular can further include a defined section of increased axial stiffness and/or longitudinal flexibility, respectively. For instance, the tip of the inner tubular member can provide an increased axial stiffness at the distal end of the distal end portion. FIG. 10A depicts the distal end of the inner tubular member 110 with a tip 61. FIG. 10B shows a representative length-stiffness graph of an example stiffness profile of the inner tubular member. The inner tubular member in this example has a tip and the stiffness of the inner tubular member is represented by the line IM. For example, the distal tip 61 can include a multi-layer construction. The multilayer tip can include a rigid material, such as, but not limited to Nylon (L25) and a flexible material. The rigid material can provide infrastructure for the catheter during multiple lesion crossings. In one embodiment, the tip can be laser welded to the inner tubular member.

The outer tubular member can also include a stiffness and/or flexibility profile along the length thereof. A plurality of factors can also affect the stiffness and/or flexibility of the outer tubular member, including, but not limited to, the materials of construction, the thickness, markers, tips, and the like. The outer tubular member can include a defined section of increased axial stiffness and/or flexibility. For instance, the tip of the outer tubular member can increase the axial stiffness of the outer tubular member. The plurality of factors can together comprise the stiffness profile of the outer tubular member. FIG. 10B shows a representative length-stiffness graph of an example stiffness profile of the outer tubular member. As depicted in FIG. 10A, the outer tubular member in this example has a tip and the stiffness of the outer tubular member is represented by the line OM. The tip of the outer tubular member can elongate the distal end of the catheter to enhance positioning of the outer tubular member for better lesion crossing.

In accordance with the disclosed subject matter, the stiffness profile of the catheter as a whole can be a function of the stiffness profile of the inner tubular member, the stiffness profile of the outer tubular member, and the selected position of the outer tubular member relative the inner tubular member. The catheter stiffness profile can vary based on the selected position of the outer tubular member relative the inner tubular member. For a given selected position of the outer tubular member relative the inner tubular member, the catheter stiffness profile can change as needed and desired, in vivo.

Figure 10C:
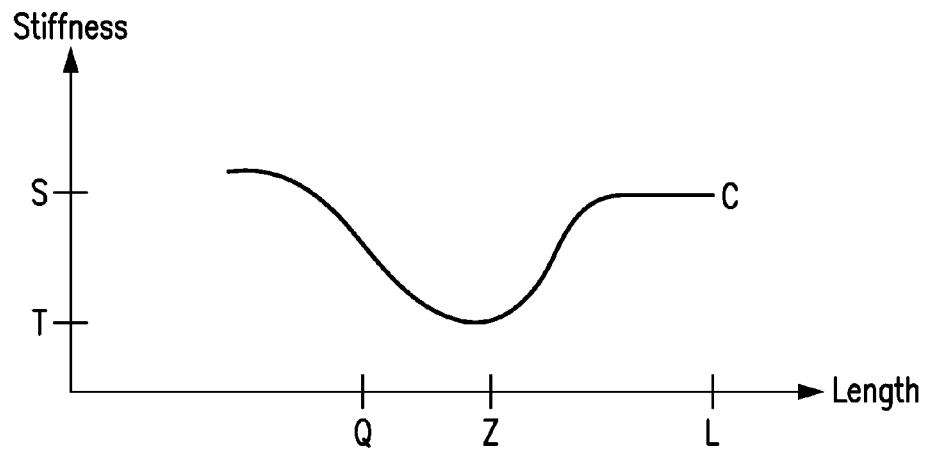
FIG. 10C shows a resulting length-stiffness graph of the catheter of FIG. 10A, in accordance with an embodiment of the disclosed subject matter.

FIG. 10C shows a length-stiffness graph of an example stiffness profile of the catheter having the stiffness profile of the inner tubular member and the stiffness profile of the outer tubular member as depicted in FIG. 10A. In this embodiment, for illustration and not limitation, the outer tubular member is in the extended position such that the length of the outer tubular member is equal to the length of the inner tubular member at position L, as depicted in the graph of FIG. 10B. The line C of FIG. 10C represents the combination of the first stiffness profile (stiffness profile of the inner tubular member) with the second stiffness profile (stiffness profile of the outer tubular member). In this embodiment, the outer tubular member is in the extended position. At a given position along the length of the catheter, the catheter will have a given stiffness based on the graph of FIG. 10C. The selected position of the outer tubular member can control the given stiffness of the catheter. In the embodiment of FIGS. 10A and C, the outer tubular member is in the extended position and the catheter has the stiffness profile as shown in FIG. 10C. For example, but not limitation, in relation to FIG. 10C, at position Q along the length of the catheter, the catheter according to this example has a stiffness of T as the outer tubular member remains at length L. However, when at length Z of the catheter, the catheter has a stiffness of S. The line C further demonstrates the change in stiffness between lengths Q and Z.

Figure 11A:
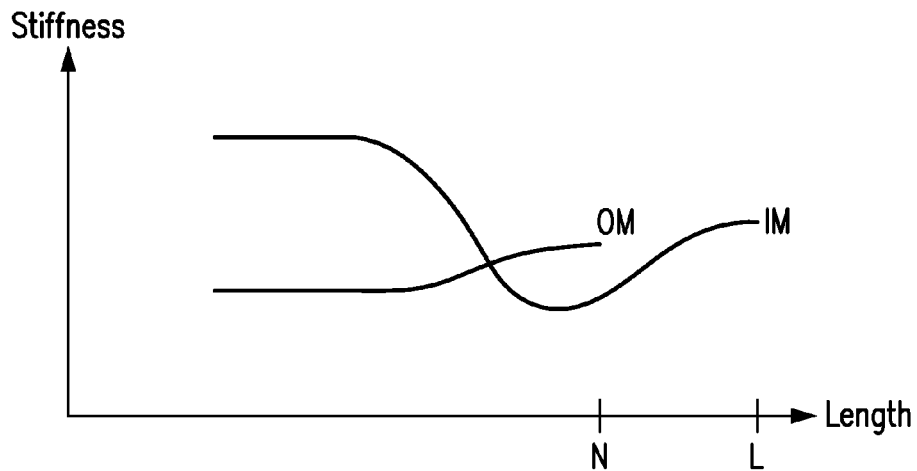
FIG. 11A shows a distal end section of the catheter of FIG. 10A with the outer tubular member partially retracted, in accordance with an embodiment of the disclosed subject matter.
Figure 11B:
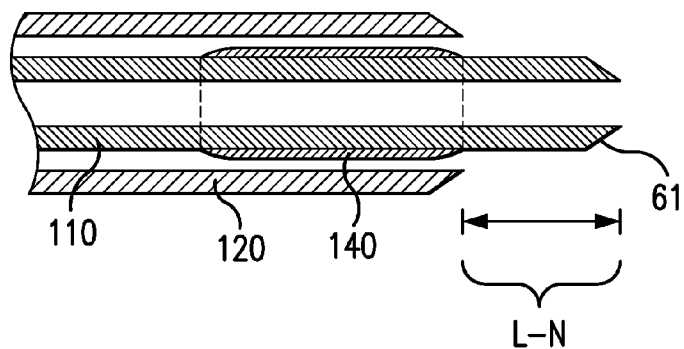
FIG. 11B shows the representative length-stiffness graph of the inner tubular member and the outer tubular member, respectively, of the catheter of FIG. 11A, in accordance with an embodiment of the disclosed subject matter.

FIG. 11A depicts the catheter of FIG. 10A, with the outer tubular member retracted a distance L-N. FIG. 11B depicts the length-stiffness graph of the inner tubular member and the outer tubular member of FIG. 10A, wherein the selected position of the outer tubular member is changed accordingly. As represented by the line OM of FIG. 11B, the outer tubular member is retracted in relation to the inner tubular member to position N. The inner tubular member of FIG. 11B remains in the same position as the inner tubular member was positioned in FIG. 10B at position L. The distal end of the outer tubular member 120 is retracted to a proximal end of the expandable member 140, as depicted in FIG. 11A.

Figure 11C:
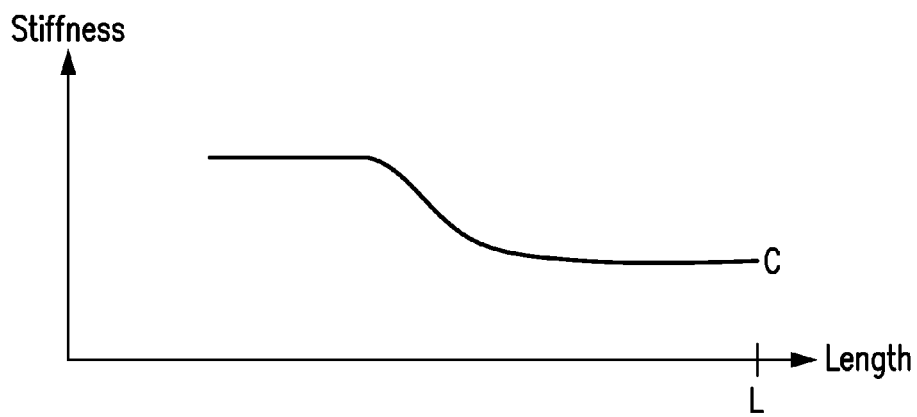
FIG. 11C shows a resulting length-stiffness graph of the catheter of FIG. 11A, in accordance with an embodiment of the disclosed subject matter.

FIG. 11C shows the length-stiffness graph of the catheter as depicted in FIG. 11A. The line C of FIG. 11C represents the combination of the first stiffness profile (stiffness profile of the inner tubular member) with the second stiffness profile (stiffness profile of the outer tubular member) as the outer tubular member is retracted to position N. At a given position along the length of the catheter, the catheter will have a given stiffness based on the graph of FIG. 11C when the outer tubular member is at position N. In contrast to FIG. 10C, FIG. 11C does not exhibit a reduced stiffness or change for line C. The selected position of the outer tubular member can control the given stiffness of the catheter.

Figure 12A:
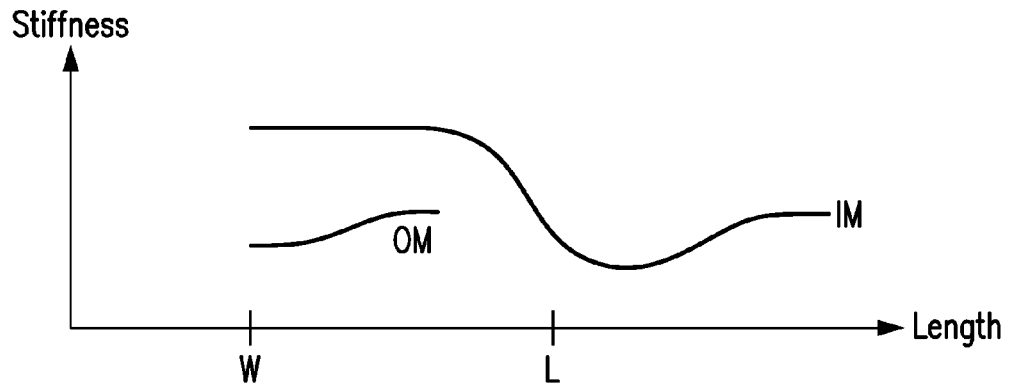
FIG. 12A shows a distal end section of the catheter of FIG. 10A with the outer tubular member further retracted, in accordance with an embodiment of the disclosed subject matter.
Figure 12B:
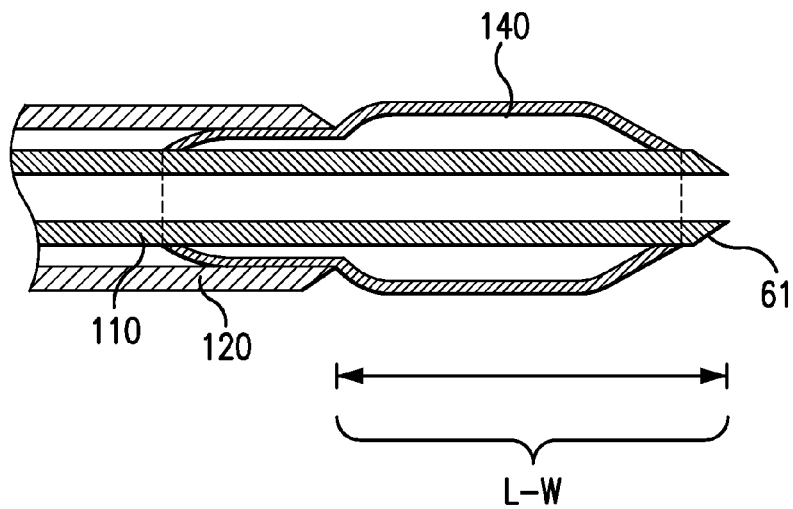
FIG. 12B shows a representative length-stiffness graph of the inner tubular member and the outer tubular member respectively, of the catheter of FIG. 12A, in accordance with an embodiment of the disclosed subject matter.

FIG. 12A depicts the catheter of FIG. 10A, wherein the outer tubular member has retracted a further distance in relation to the inner tubular member. FIG. 12B depicts another length-stiffness graph of the inner tubular member and the outer tubular member of FIG. 10A, wherein the selected position of the outer tubular member has further changed accordingly. As represented by the line OM of FIG. 12B, the outer tubular member is retracted in relation to the inner tubular member to position W. The inner tubular member of FIG. 11B remains in the same position as the inner tubular member was positioned in FIGS. 10A and 10B at position L. The distal end of the outer tubular member 120 is retracted to a distal end of the expandable member 140, as depicted in FIG. 12B.

Figure 12C:
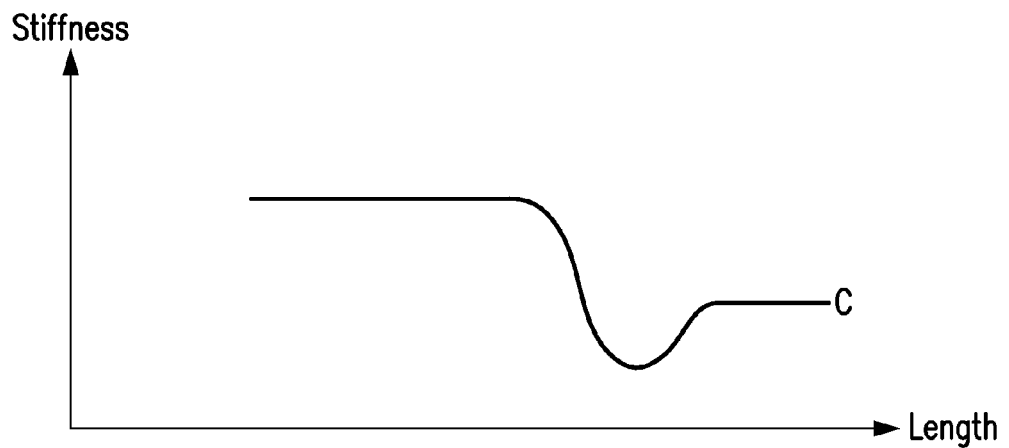
FIG. 12C shows the resulting length-stiffness graph of the catheter of FIG. 10A, in accordance with an embodiment of the disclosed subject matter.

FIG. 12C shows the length-stiffness graph of the catheter as depicted in FIG. 12A. The line C of FIG. 12C represents the combination of the first stiffness profile (stiffness profile of the inner tubular member) with the second stiffness profile (stiffness profile of the outer tubular member) as the outer tubular member is retracted to position W. At a given position along the length of the catheter, the catheter will have a given stiffness based on the graph of FIG. 12C when the outer tubular member is at position W. In FIG. 12C, the line C exhibits a high constant stiffness over a longer period of time and has a higher gradient exhibiting a decrease in stiffness, as opposed to FIGS. 10C and 11C. The selected position of the outer tubular member can control the given stiffness of the catheter. Accordingly, a physician can alter the stiffness of the catheter stiffness profile in vivo based on the selected position of the outer tubular member relative the inner tubular member.

Similarly, as previously discussed, the adjustable balloon catheter can further have a flexibility profile based on the flexibility of the catheter. For instance, the inner tubular member can have a flexibility profile along the length thereof. A plurality of factors can affect the flexibility of the inner tubular member including, but not limited to, the materials of construction of the inner tubular member, the thickness of the inner tubular member, the application of radiopaque markers, the application of an inner tubular member tip, and other applicable factors. As desired, and in accordance with another aspect herein, the inner tubular member can further have a defined section of increased longitudinal flexibility. The plurality of factors together define the flexibility profile of the inner tubular member.

The outer tubular member can also include a flexibility profile along the length thereof. A plurality of factors can also affect the flexibility of the outer tubular member, including, but not limited to, the materials of construction, the thickness, markers, tips, and the like. The outer tubular member can have a defined section of increased longitudinal flexibility. The plurality of factors together define the flexibility profile of the outer tubular member.

In accordance with the disclosed subject matter, the flexibility profile of the catheter can be a function of the flexibility profile of the inner tubular member, the flexibility profile of the outer tubular member, and the selected position of the outer tubular member relative the inner tubular member. The catheter flexibility profile can vary based on the selected position of the outer tubular member relative the inner tubular member. For a given selected position of the outer tubular member relative the inner tubular member, the catheter flexibility profile can change as needed and desired, in vivo.

In accordance with the disclosed subject matter, the inner and/or outer tubular member can be provided with defined sections of increased flexibility or stiffness (i.e., durometer) along its length. This can be accomplished in a variety of suitable ways, as further discussed below.

Figure 13A:
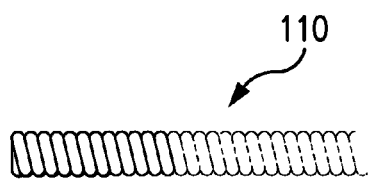
FIGS. 13A-13G are schematic side views in partial cross-section of various embodiments of the inner tubular member, in accordance with an embodiment of the disclosed subject matter.
Figure 13B:
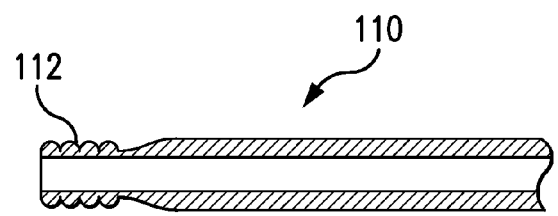

In one aspect of the disclosed subject matter, the inner tubular member can be reinforced to provide higher stiffness of the inner tubular member and thus provide a higher stiffness of the catheter itself. For example, at least a portion of the inner tubular member includes a coiled construction, as depicted in FIG. 13A. The coiled construction can further include a crimp at an end of the inner tubular member. The crimp can further stabilize the outer diameter of the tubular member. FIG. 13B depicts the inner tubular member having a coiled construction with a crimp 112 at an end of the inner tubular member. The coiled construction can include a metallic material, such as but not limited to, stainless steel including 302, 304V, 316L; 35N LT®; CP Titanium; Pt Alloys; DFT®; Ti 6Al-4V ELI; L-605; and Nitinol.

Figure 13C:
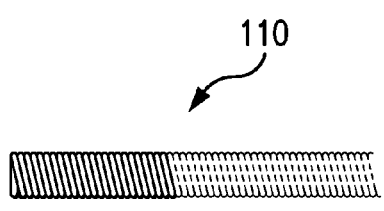
Figure 13D:
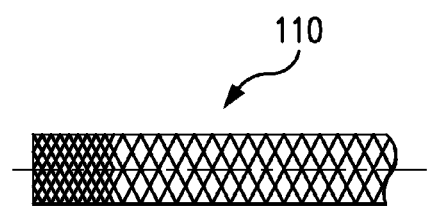
Figure 13E:
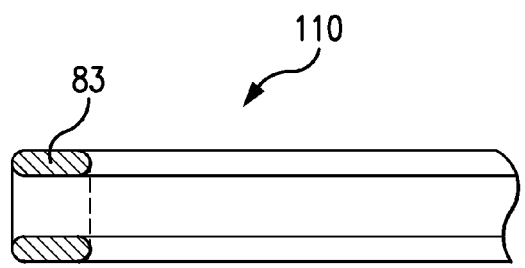
Figure 13F:
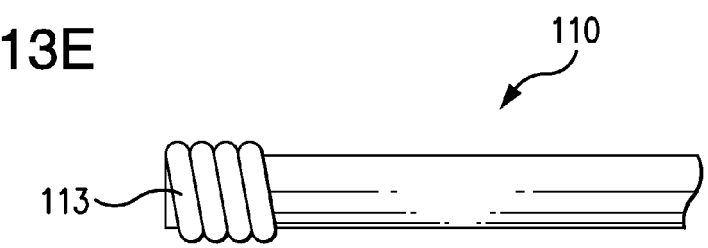

The coiled construction can further include a multi-coil construction for the inner tubular member for even greater stiffness and/or flexibility. FIG. 13C depicts the inner tubular member having a multi-coil construction. In one embodiment, at least a portion of the coiled construction can be made of radiopaque material. In another embodiment, at least a portion of the inner tubular member includes a braided construction. The braided construction can also include a metallic material, such as but not limited to, stainless steel including 302, 304V, 316L; 35N LT®; CP Titanium; Pt Alloys; DFT®; Ti 6Al-4V ELI; L-605; and Nitinol. The braided construction can have a higher density at a distal segment of the distal end portion of the inner tubular member and the higher density can function as a marker, as depicted in FIG. 13D. In another embodiment, coil element 113 or a coil tube can be disposed at the distal end thereof, as depicted in FIG. 13F.

In accordance with another aspect of the disclosed subject matter, for purpose of illustration and not limitation, at least a portion of the inner tubular member can include a hypotube 114. For purposes of illustration and not limitation, the hypotube can be made of suitable material, such as stainless steel or Nitinol. For increased flexibility, the hypotube can include one or more cuts or slits, such as formed by a laser, to define flexible hinge-like regions as disclosed in U.S. Pat. Nos. 7,780,716; 7,794,489; and 7,799,065; which are incorporated by reference herein in their entirety. The hypotube can include a marker 83 at the distal end thereof as depicted in FIG. 13E.

According to another embodiment of the disclosed subject matter, at least a portion of the inner tubular member can further include a tapered shaft. The tapered shaft can increase flexibility and improve overall pushability of the catheter. According to another embodiment, the inner tubular member can include a compound shaft material as known in the art.

Figure 13G:
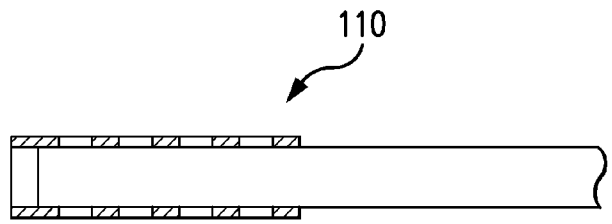
Figure 14:
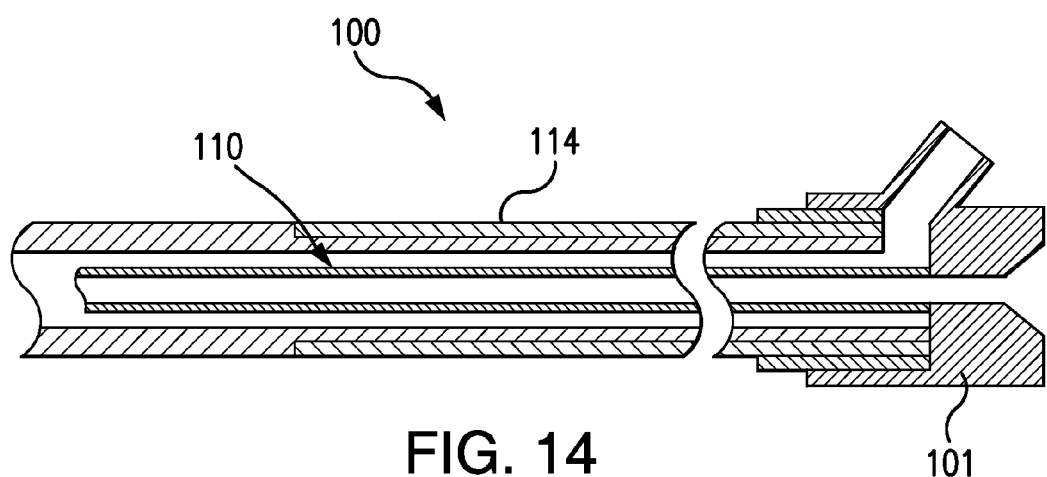
FIG. 14 is a schematic cross sectional side view including an embodiment of the proximal end of a catheter in accordance with the disclosed subject matter.

In FIG. 14, the proximal end of a balloon catheter is depicted. In this embodiment, the proximal end includes a hypotube reinforcement to increase stiffness at the proximal end of the catheter. The increased stiffness at the proximal end of the catheter can increase the pushability during insertion into a patient's luminal system. For example, and not limitation, a catheter for peripheral vascular use can include a hypotube and can have a length of approximately 250 mm. In a further embodiment, the tube can include synthetic materials, as depicted in FIG. 13G. Spirals and cuts can be employed to transition from any type of reinforcement or hypotube to an adjacent structure, such as a polymer tube. Other reinforcement techniques known in the art can also be used.

Figure 15A:
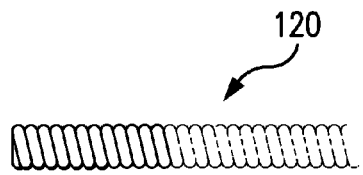
FIG. 15A-15D are various embodiments of the outer tubular member, in accordance with an embodiment of the disclosed subject matter.
Figure 15B:
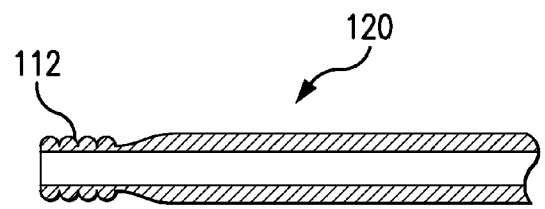
Figure 15C:
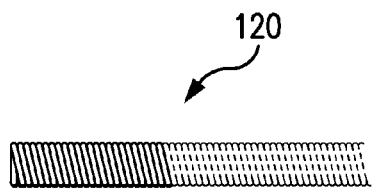

In another aspect of the disclosed subject matter, the outer tubular member can be further reinforced to provide higher stiffness of the outer tubular member and thus provide a higher stiffness of the catheter itself. In one embodiment, at least a portion of the outer tubular member includes a coiled construction. For example, but not limitation, a catheter can include an outer tubular member including a coiled construction. FIG. 15A depicts the outer tubular member having a coiled construction. The coiled construction can be disposed at the distal end of the outer tubular member. The coiled construction can include a variety of suitable materials, such as but not limited to, stainless steel including 302, 304V, 316L; 35N LT®; CP Titanium; Pt Alloys; DFT®; Ti 6Al-4V ELI; L-605; and Nitinol. The coiled construction of the outer tubular member can further include a crimp 122 as depicted in FIG. 15B. The coiled construction can further include a multi-coil construction for the outer tubular member for even greater stiffness. FIG. 15C depicts the outer tubular member having a multi-coil construction.

Figure 15D:
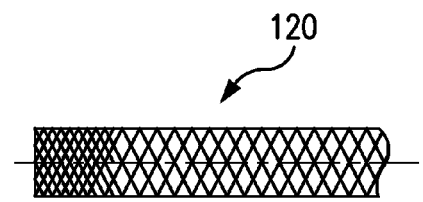

In another embodiment and as provided in FIG. 15D, at least a portion of the outer tubular member includes a braided construction. For example, but not limitation, a 014 catheter system can include an outer tubular member with a braided construction. The braided construction can also include a metallic material, such as but not limited to, stainless steel including 302, 304V, 316L; 35N LT®; CP Titanium; Pt Alloys; DFT®; Ti 6Al-4V ELI; L-605; and Nitinol. In other embodiments, the outer tubular member does not include a braided configuration.

In another embodiment, the material construction of the outer tubular member can be varied to further provide stiffness of the outer tubular member and thus provide stiffness for the catheter itself For example, a proximal portion of outer tubular member embodied herein can include a first material and the distal portion of outer tubular member can include a second, different material at its distal end. The outer tubular member can also define an intermediate region wherein the first material is blended with the second material. For example, the first material can be a first polymer material and the second material can be a second, different polymer material.

In accordance with an embodiment of the disclosed subject matter, the distal portion of the outer tubular member can have a length of ranging between approximately 75-125 mm for use in peripheral vascular indications, and outer tubular member can have a total length of up to about 1200 mm. It is understood that the dimensions of the outer tubular member will depend on the intended application. The second polymer material incorporated into distal portion of the outer tubular member can be less stiff than the first polymer material in proximal portion of the outer tubular member. For example, the first polymer material can include NYLON 12 and the second polymer material can include NYLON 68D. Other polymer materials however, can be used in lieu of or in combination with the above-described materials. For example, a block copolymer material such as PEBAX® 7233 can be used. Alternatively, other materials such as polyvinylchloride (PVC) or polyurethanes can be used.

Variation in stiffness or flexibility can be predetermined by blending the materials in varying proportions along the length of the outer tubular member such that the majority of material at the proximal end of the outer tubular member is NYLON 12 and the majority of material at distal end of the outer tubular member is NYLON 68. It is also within the scope of the disclosed subject matter to vary the rigidity of the outer tubular member by varying the diameter along the outer tubular member.

In accordance with another aspect of the disclosed subject matter, the inner tubular member and/or the outer tubular member can each include a distal tip configuration.

Figure 16:
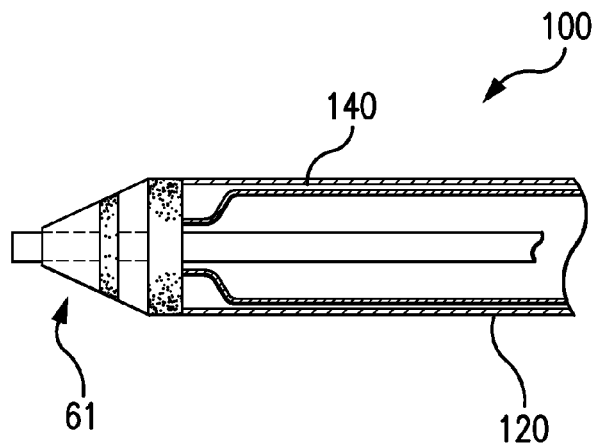
FIG. 16 and FIG. 17 are schematic views of the distal end section of a catheter with the outer tubular member in the extended position and the retracted position, respectively, wherein the outer tubular member has a distal marker, in accordance with an embodiment of the disclosed subject matter.
Figure 17:
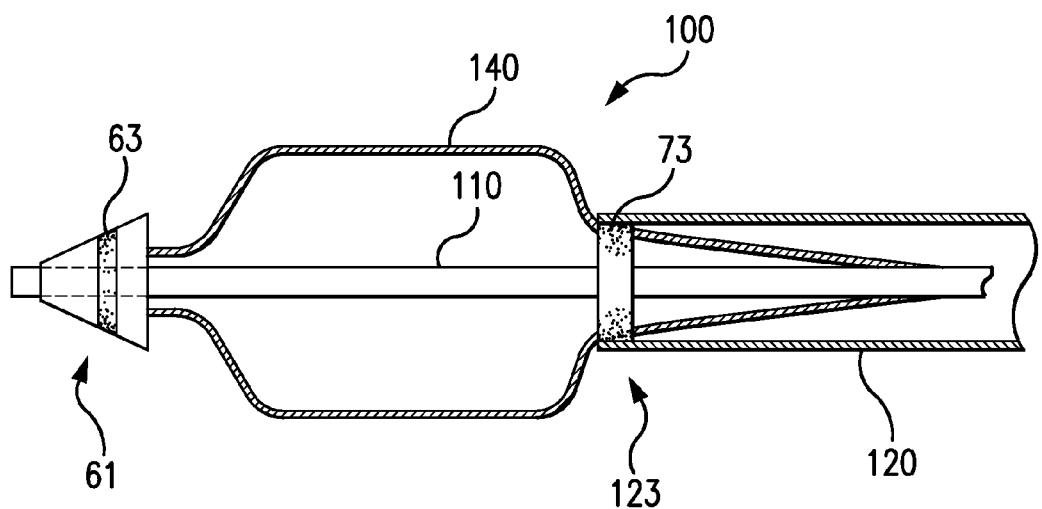

In accordance with another aspect of the disclosed subject matter referring to FIGS. 16 and 17, for purpose of illustration and not limitation, an embodiment of a balloon catheter in accordance with the disclosed subject matter is depicted in its delivery configuration with the outer tubular member fully extended, and in its expanded configuration with the outer tubular member retracted, respectively. The distal end 123 of the outer tubular member and the distal tip 61 of the inner tubular member each include a marker. The distal tip 61 of the inner tubular member can include a radiopaque marker 63 to enhance visibility of the distal tip within a patient's vasculature, as further described herein. The distance between the marker of the inner tubular member and marker of the outer tubular member when the outer tubular member is retracted indicates the working length of balloon that is exposed.

Alternatively or additionally, a scale or markers can be disposed on the proximal end of the catheter to aid in length adjustment, as further discussed herein. The distal tip can be constructed of a soft polymer material which includes tungsten as the marker. The soft tip can prevent damage to the vessel walls while the catheter is within a patient's vasculature.

Figure 18:
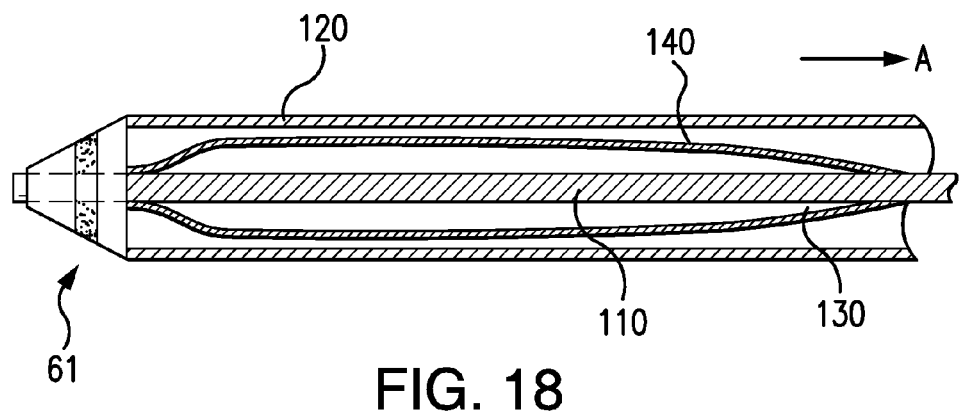
FIG. 18 and FIG. 19 are schematic side views in partial cross-section of embodiments of the distal tip of a catheter in the retracted position and in the extended position, respectively in accordance with the disclosed subject matter.
Figure 19:
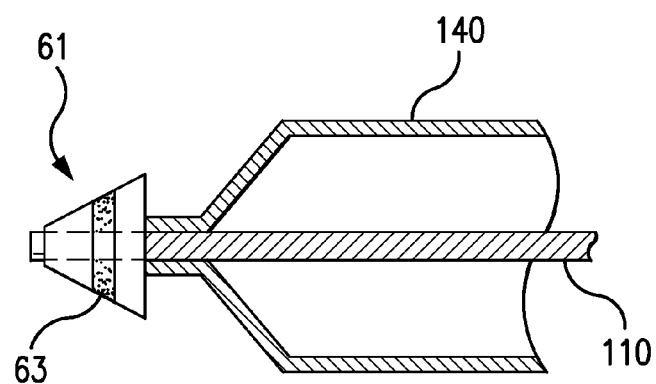

Further, for purpose of illustration and not limitation, FIG. 18 depicts the expandable member in a deflated configuration with the outer tubular member fully extended. In this embodiment, the outer tubular member does not include a tip and the outer tubular member does not include a marker at the distal end. In this embodiment, the distal tip of the inner tubular member is sized to engage against the outer tubular member and prevent over-extension of the outer tubular member distally. FIG. 19 depicts the expandable member in the inflated configuration with the outer tubular member retracted. The distal tip, as shown, also can provide a seal preventing or decreasing the exposure of the expandable member to the patient's blood until the catheter is at the treatment site and the outer tubular member is retracted. The distal tip as embodied herein also provides a smoother transition between the proximal end of the tip and the distal end of the outer tubular member. In another embodiment, the distal tip can be formed by rounding of the distal end of the inner tubular member. This reduces loss of therapeutic agent, if applied to the expandable member.

Figure 20A:
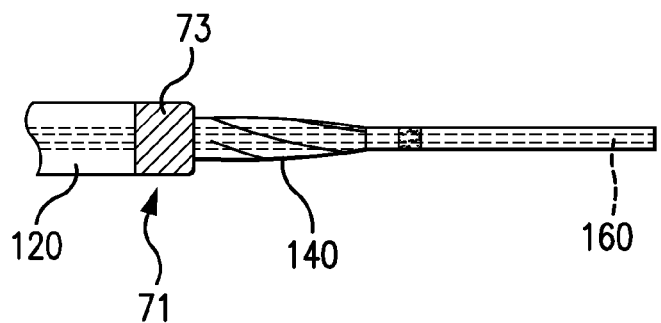
FIGS. 20A-20C are schematic images of alternate embodiments of distal tips of a catheter in accordance with the disclosed subject matter.
Figure 20B:
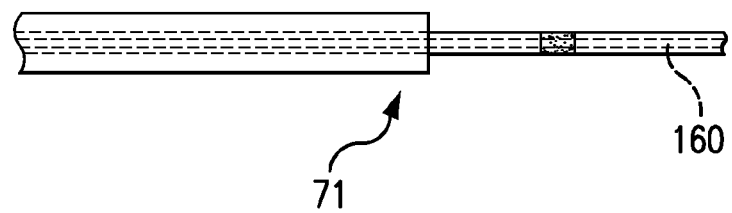
Figure 20C:
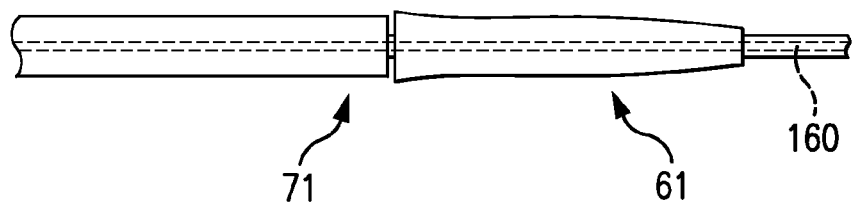

In another embodiment, the outer tubular member includes a distal tip at the distal end thereof. FIG. 20A depicts the distal tip 71 of the outer tubular member with a metal marker 73 on the distal end of the outer tubular member 120. In this embodiment, the inner tubular member 110 does not include a tip at a distal end thereof. FIG. 20B depicts the distal tip 71 of the outer tubular member wherein the distal end of the outer tubular member includes a soft tip with a marker. As discussed above, one method of achieving the depicted configuration is through the use of tungsten loaded polymers. In other embodiments of the disclosed subject matter, both the inner tubular member and the outer tubular member can include distal tips, respectively. FIG. 20C depicts the distal tip 61 of the inner tubular member and the distal tip 71 of the outer tubular member, both of which can include markers and can be soft at their respective distal ends. The tips of the inner tubular member and the outer tubular member can contribute to the stiffness or flexibility of the catheter, as previously discussed herein.

In accordance with one aspect of the disclosed subject matter, the adjustable balloon catheter 100 can include a plurality of radiopaque markers. The markers can be placed in a variety of suitable locations along the catheter including, but not limited to, the inner tubular member, the outer tubular member, and the expandable member.

Figure 21:
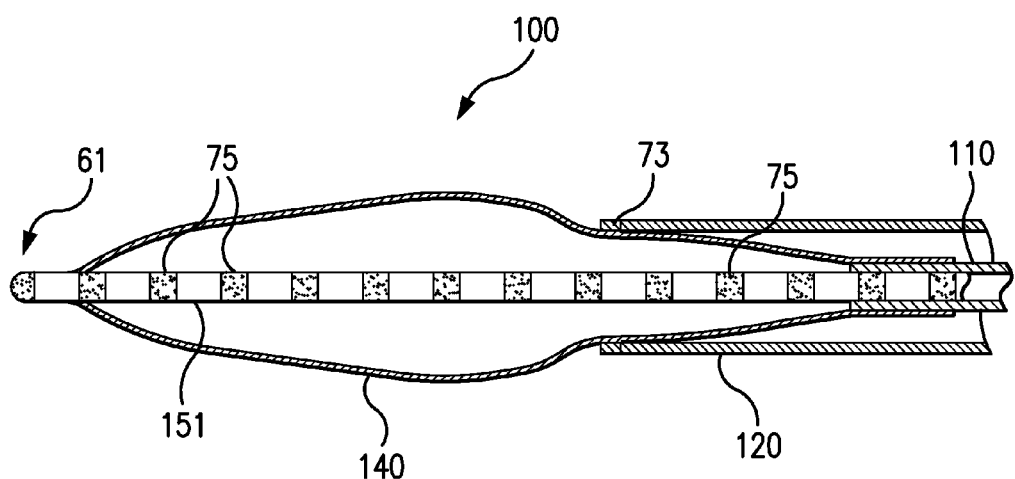
FIG. 21 is a schematic cross-sectional side view of the distal end of the catheter having gradient markers in accordance with another embodiment of the disclosed subject matter.

Reference is made to FIG. 21 for purpose of illustration and not limitation, which depicts an embodiment of the distal end of the adjustable balloon catheter. FIG. 21 depicts a plurality of markers distributed along the adjustable length catheter. The distal tip 61 of the inner tubular member includes a radiopaque marker 63. Further, as shown, the inner tubular member includes at least one proximal marker proximal to the distal marker. In the embodiment of FIG. 21, radiopaque markers extend from the distal end of the inner tubular member, along the length towards its proximal end. The markers 75 can extend along a portion of the inner tubular member within the expandable member. At least one proximal marker can be located proximate a center of the working length of the expandable member. The markers can continue to the proximal end of the inner tubular member including markers on the hypotube, if provided. In this embodiment, the outer tubular member includes a marker 73 at the distal end thereof. The marker 73 can be positioned at a tip of the outer tubular member or independent of any tip at the outer tubular member. In embodiments where the inner tubular member includes a coiled construction as discussed below, a radiopaque marker can be provided with the coiled construction or at least a portion of the coiled construction can be made of radiopaque material. The marker in this embodiment can be a separate radiopaque member attached to the member, or can be applied by any suitable method, including but not limited to, a vapor depositing process, as known in the industry.

In one embodiment, the radiopaque markers are strategically spaced a predetermined distance apart from each other to gauge the working length of the expandable member. The markers are spaced at known increments from each other allowing a physician to determine the exact length of the expandable member that is exposed and to determine the location of other portions of the catheter. For example, each radiopaque marker can be spaced approximately 10 mm apart along a portion of the inner tubular member. Additionally, or alternatively, gradients or similar indicia can provided on the proximal end of the adjustable balloon catheter to identify the distance in which the outer tubular member has been retracted and thus the exposed length of the expandable member.

Figure 22:
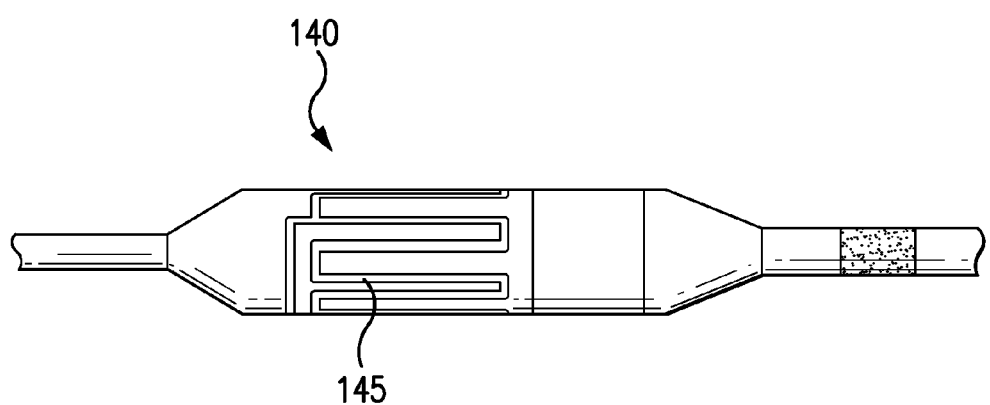
FIG. 22 is a schematic side view of a distal end of the catheter with the expandable member with an alternative marker arrangement, in accordance with an embodiment of the disclosed subject matter.

The expandable member can also include markers. The markers can be positioned at a plurality of suitable locations, including, but not limited to, the distal end of the expandable member and the proximal end of the expandable member. In one embodiment, a radiopaque marker 145 is applied to the exterior of the expandable member with a pattern to define a length, diameter or other characteristic when inflated, as depicted in FIG. 22. The marker in this embodiment can be applied by a vapor depositing, as known in the industry.

The markers can include any suitable material. For example, the markers can be constructed of a polymer filled or impregnated with a radiopaque material and can further include, but not limited to, PPS, Tungsten, and glass fiber combination; PA12 and ceramics combination; PEEK and ceramics combination; and a PBT and ceramics combination.

In accordance with an embodiment of the disclosed subject matter, a method of deploying a medical device is provided. The method includes providing an adjustable balloon catheter including any of a combination of the features as previously described. The method further includes inserting the catheter into a body lumen of a patient and retracting the outer tubular member in a proximal direction to define the exposed length of the working length of the expandable member. The retracting can further include selecting the exposed length of the expandable member such that an outer diameter of the expandable member is selectively determined by the outer tubular member. The exposed length of the expandable member is inflated to the inflated configuration, such as by introducing fluid into the inflation lumen. The expandable member is deflated to the deflated configuration and withdrawn from the body lumen of a patient.

Accordingly, a physician can selectively expose as much of the balloon as needed in order to perform the desired treatment. Thus, in accordance with the disclosed subject matter, a physician can treat a vascular section of varying length using an expandable member or balloon of one length by selectively exposing the desired length as shown in FIGS. 24A-D for the purpose of illustration and not limitation. The additional aspects and benefits of the method performed using the catheter as disclosed are evident and described in detail in conjunction with the various features of the device.

The inner and outer tubular members of the adjustable balloon catheter each can be single piece construction, or an assembly of components, and can be made of any suitable material. For example, suitable materials include, but are not limited to polymer materials such as nylon, urethane, polyurethane, PEEK, PTFE, PVDF, Kynar, PE, HDPE, a trilayer material including L25, Plexar, or polyethylene of various suitable densities. As a further exemplary alternative, the outer tubular members can be constructed of a composite comprising a fabrication of several different materials, such as a co-extrusion of different polymers, or a fiber-reinforced composite material such as fiber reinforced resin materials or braided materials. For example and not limitation, exemplary embodiments can include a braided tube with a PTFE liner, a Polymide middle layer with braiding and a Pebax 72D outer layer, as previously described. Furthermore, a portion of the inner and/or outer tubular members can be constructed of an alloy or metallic material, such as stainless steel hypodermic tubing which is available from MicroGroup® Inc., Medway, Md. among other vendors. Other materials for the outer tubular member include PEEK; a trilayer material of L25, Plexar, HDPE; or a braided tube with a PTFE liner, a Polyimide middle layer with braiding and a Pebax 72D outer layer.

It is further contemplated that the inner and outer tubular members can be constructed of other biocompatible material. As such, the inner and outer tubular members of the adjustable balloon catheter can be constructed from the above-identified polymers, combinations or blends of these polymers, whether alone or in combination with other materials, or other bioabsorbable materials.

The inner and outer tubular members can be manufactured using a variety of known techniques such as, but not limited to, those techniques previously discussed and extrusion, injection molding, air-blowing, stretching, deep drawing, polymerization, cross-linking, dipping from solution, powder depositioning, sintering, electro-spinning, melt spinning, deformation under temperature, stretch blowing, chemical grafting any combination of the above with reinforcement element like metal braids, coils, glass fibers, carbon fibers and other kind of organic or inorganic fibers, liquid crystals, as well as classical machining technologies like milling, drilling, grinding, etc. In the event that metallic elements such as hypotubes, are to be incorporated, various metallic manufacturing techniques can be used, such as but not limited to, machining, tube drawing processes, drilling, milling EDM, other deformation methods, plating sputtering, electrografting, sintering, and depositioning e-polishing, among others. Additionally, the inner and/or outer tubular members can be constructed from polypropylene or urethane by an extrusion process using an extruder such as that available any of a number of known suppliers, such as Medical Extrusion Technologies, Inc. Murrieta, Calif. U.S. Biosynthetic polymer materials can be constructed in a bioreactor according to the process disclosed in U.S. Pat. No. 6,495,152, the entirety of which is hereby incorporated by reference. The materials can be post processed in a number of ways including, for example and not by way of limitation, extrusion, molding, such as by injection or dipping, textile processing such as weaving or braiding, and forming. Forming processes that can be suitable are rolling and welding sheets of material or vacuum forming into tubular shapes, to name only a few examples.

The inner and outer tubular members can be further coated with any of a variety of materials and techniques to enhance performance if desired, including a number suitable coatings and coating techniques subject to patent matters owned by Abbott Laboratories such as U.S. Pat. Nos. 6,541,116, 6,287,285, and U.S. Patent Publication No. 2002/0009535, the entireties of which are hereby incorporated by reference. For example, possible coating materials include lubricious materials such as Teflon® available from DuPont De Nemours, Wilmington, Del., U.S., and hydrophobic materials such as silicone lubricant dispersion PN 4097, available from Applied Silicone Corp., Ventura, Calif., U.S., or hydrophilic materials such as hydrogel available from Hydromer, Branchburg, N.J., U.S., or lubricious coatings such as those available from Hydro-Silk of Merritt Island, Fla., U.S. The inner and outer tubular members can have any suitable cross-sectional shape, including elliptical, polygon, or prismatic, although a circular cross-section is common. The inner and outer tubular members can also have any suitable size and diameter depending upon the desired application. Furthermore, in the case of a balloon catheter with a "rapid exchange" (RX) guidewire design, the adjustable balloon catheter can have an overall length between about 110 centimeters and 400 centimeters. In the case of a balloon catheter with an "over the wire" (OTW) guidewire design, the adjustable balloon catheter can have an overall length between about 110 centimeters and 400 centimeters. In one embodiment, the adjustable balloon catheter in accordance with the disclosed subject matter is a compatible 4 French introducer sheath BTK balloon device.

Figure 23A:
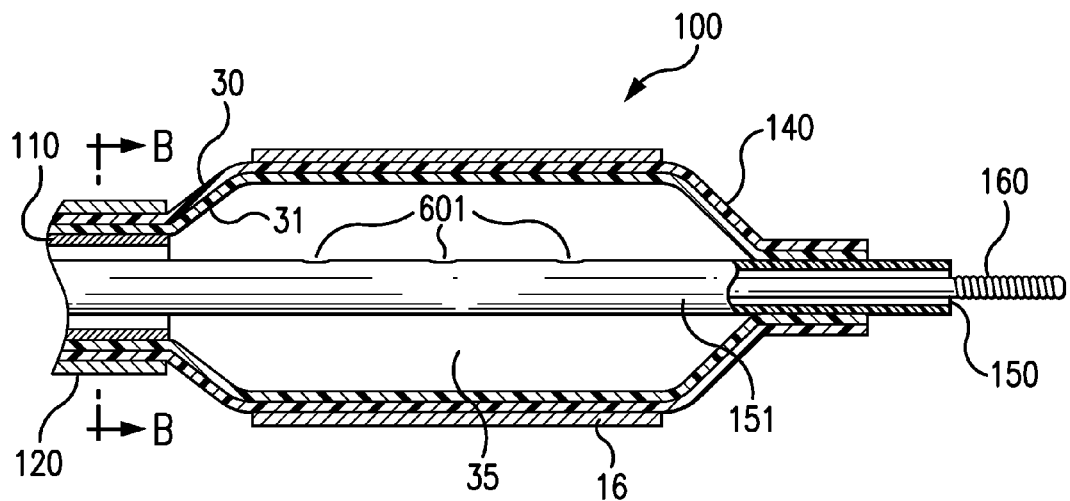
FIG. 23A is a schematic cross-sectional side view of a multi-layer balloon in accordance with an embodiment of the disclosed subject matter.
Figure 23B:
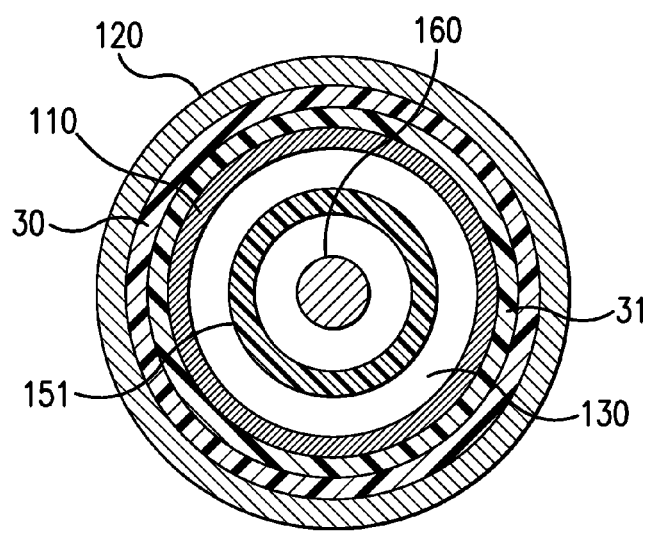
FIG. 23B is a cross sectional view of the catheter of FIG. 23A taken along line B-B.

As previously disclosed, the expandable member can have a multilayered construction. For purposes of illustration and not limitation, FIGS. 23A and 23B illustrate a balloon catheter with the balloon 140 in the inflated configuration to expand against a wall of a body lumen. The outer tubular member 120 defines the length of the balloon 140, as depicted in FIG. 23A although the working length could be less than the entire length. For example, as previously noted, the outer tubular member can be configured as a stop mechanism to ensure the proximal end portion remains within the outer tubular member. When treatment is complete, the balloon 140 is then deflated to allow for repositioning or removal of the catheter from the body lumen. FIG. 23B illustrates, for the purpose of illustration and not limitation, a transverse cross section of the catheter of FIG. 23A, taken along line B-B.

Although not illustrated, the balloon 140 of the disclosed subject matter can have a folded non-inflated configuration with wings wrapped around the balloon to form a low profile configuration for introduction and advancement within a patient's body lumen. As a result, the balloon inflates to a nominal working diameter by unfolding and filling the molded volume of the balloon.

As shown in FIG. 23A, for the purpose of illustration and not limitation, the balloon 140 has a first layer 30, and a second layer 31 which is an inner layer relative to the first layer 30. In the illustrated embodiment, the second layer 31 is on an inner surface of the first layer 30, with the first layer 30 defining an outer surface of the balloon 140 and the second layer 31 defining an inner surface of the balloon 140. The first layer 30 defines the inner chamber 35 of the balloon 140. However, the balloon 140 of the disclosed subject matter can alternatively have one or more additional layers (not shown). Additional layer(s) increase the dimensions of the tube/balloon formed therefrom to a desired value, and/or can be used to provide an inner or outer surface of the balloon with a desired characteristic. Therefore, it should be understood that the balloon 140 of the disclosed subject matter has at least two layers, and optionally includes one or more additional layers.

The first (outer) layer 30 can be formed of a first polymeric material, and the second (inner) layer 31 is formed of a second polymeric material that can be expanded to a higher BUR than the first polymeric material. The second (inner) layer 31 can be at a BUR which is typically about 15% to about 40% greater than the BUR of the first (outer) layer 30. Each layer 30, 31 can be at its maximum BUR, so that the balloon has layers of highly oriented material and, consequently, a very low compliance.

A variety of suitable materials can be used to form the first and second layers 30, 31, including polyamides, polyurethanes, and polyesters, and blend thereof. In one embodiment, the first and second polymeric materials are elastomers providing a relatively low flexural modulus for balloon flexibility, although nonelastomers can alternatively be used. In one embodiment, materials are from the same polymeric family/class such as polyamides including nylons and polyether block amides (PEBAX®). Forming the layers of compatible polymeric materials allows for heat fusion bonding the layers together. The layers can alternatively be formed of different polymer classes which are not sufficiently compatible to fusion bond together, in which case a tie layer is typically provided between the outer and inner layers 30, 31 to bond the balloon layers together. For example, a PET inner layer and a PEBAX® typically have a tie layer of an adhesive polymer such as Primacor (a functionalized polyolefin) therebetween.

In accordance with one aspect of the disclosed subject matter, the balloon 140 can be formed by a method in which the layers of material that can be expanded to higher BURs are the inner layers of the balloon tubing, and lower BUR materials are the outer layers, and the balloon is blow-molded such that each layer is optimized for radial orientation. The resulting balloon has an increased resistance to radial expansion at increasing inflation pressures.

The balloon 140 can be blow-molded from a multilayered tube which has the first layer 30, and the second layer 31 as an inner layer relative to the first layer 30. However, as discussed above, a balloon of the disclosed subject matter can have one or more additional layers, so that the tubing used to blow-mold the balloon would similarly be formed with the additional layer(s). The tube is typically formed by coextrusion, although a variety of suitable method can be used. For example, in one embodiment, a multilayered tube is formed by coextruding at least two layers, and one or more additional layers are added to the coextruded tube for example by heat shrinking, dip coating, adhesive or fusion bonding, or frictionally engaging the additional layer(s) to the coextruded tube.

The multilayered tube can be then radially expanded in a balloon mold to form the balloon 140. The inner diameter of the mold typically is about equal to the nominal working diameter of the expanded balloon 140. The multilayered tube is typically stretched axially and heated during blow molding in the balloon mold, as is conventionally known. For example, in one embodiment, the tube is longitudinally stretched by about 200% during blow molding, which produces a biaxially oriented balloon. The single wall thickness of the tube (prior to being radially expanded in the mold) is about 0.1 to about 0.4 mm, and the single wall thickness of the resulting balloon (radially expanded in the mold) is about 0.01 to about 0.04 mm, depending on the desired balloon characteristics and uses.

The materials and dimensions of the multilayered tube and balloon mold can be selected so that each layer of the resulting balloon has been radially expanded to substantially its maximum possible amount, expressed as the BUR of the balloon layers. In one embodiment, the outer layer 30 has a higher Shore durometer hardness and therefore lower elongation than the one or more inner layers. The elongation of each layer is typically about 10% to about 50%, and more specifically about 20% more than the elongation of the outer layer immediately adjacent thereto.

In one embodiment, the first (outer) layer 30 is a PEBAX® having a Shore durometer hardness of about 72D, and the second (inner) layer 31 is a PEBAX® having a Shore durometer hardness of about 63D. The PEBAX®72D outer layer 30 typically has a BUR of between about 6 and 7, and the PEBAX® 63D inner layer 31 a BUR of between about 7 and 8 or 7 and 9.

In one embodiment, a mid layer (not shown) of intermediate BUR and/or durometer hardness is provided between the outer and inner layers 30, 31. For example, in one embodiment, the balloon 140 has a first, outer layer 30 of PEBAX 72D, a second, inner layer 31 of PEBAX 63D, and a midlayer (not shown) therebetween of PEBAX 70D. In one embodiment, the inner and mid layers have a smaller wall thickness than the highest durometer layer therearound, and typically together make up about 5% to about 15% of the total wall thickness of the multilayered balloon. The balloon 140 can similarly have one or more additional layers (not shown) which similarly continue the pattern of sequentially increasing BUR and/or durometer from the inner toward the outer layers of the balloon. However, in one embodiment, the balloon 140 has a relatively soft outer-most layer (not shown) having a Shore durometer hardness less than the immediately adjacent inner layer of the balloon, which can facilitate embedding a stent 16 (shown in FIG. 23A) into the outer surface of the balloon for improved stent retention. Such a relatively soft outer-most layer typically has of a relatively low Shore durometer hardness of about 40D to about 55D.

The multilayered balloon of the disclosed subject matter has a low compliance, and a relatively high rupture pressure, particularly when compared to a balloon of otherwise similar construction but formed solely of the highest durometer material used to make the multilayered balloon of the disclosed subject matter (e.g., a 72D PEBAX® outer layer of multilayered balloon 140), or compared to a balloon formed of layers of different durometer materials but not layered in accordance with the disclosed subject matter. The compliance is typically determined for the pressure range extending from the nominal pressure (i.e., the pressure required to fill the molded volume of the balloon to the blow-molded nominal diameter) to the burst pressure or the rated burst pressure of the balloon. The rated burst pressure (RBP), calculated from the average rupture pressure, is the pressure at which 99.9% of the balloons can be pressurized to without rupturing, with 95% confidence.

In accordance with one aspect of the disclosed subject matter, the multilayered balloon 140 has a nominal pressure of about 6 to about 12 atm, and more typically of about 7 to about 9 atm, and a RBP of about 14 to about 22 atms, more typically about 18 to about 20 atms. The rupture pressure is typically about equal to, greater than, or not substantially less than (i.e., not more than about 5% to about 15% less than) a rupture pressure of a balloon of otherwise similar construction but formed solely of the highest durometer material.

In one embodiment, a multilayered balloon of the disclosed subject matter having at least a 72D PEBAX® outer layer and a 63D PEBAX® inner layer reaches the nominal diameter of the balloon at about 8 to about 9 atm, and thereafter stretches in a noncompliant manner with a compliance of about 0.01 to about 0.02 mm/atm within the working pressure range (e.g., 8-20 atm) of the multilayered balloon to a diameter which is not more than about 8% greater than the nominal diameter.

Due to the presence of the softer durometer inner layer(s), the flexural modulus of a multilayered balloon of the disclosed subject matter is expected generally to be about 90% to about 95% of the flexural modulus of a balloon consisting of the first (e.g., higher durometer) elastomeric polymeric material of the layer 30. Additional details and examples of suitable multilayer balloons for use in the disclosed subject matter are described in U.S. Pat. No. 7,828,766, the contents of which is incorporated herein in its entirety.

A wide variety of suitable materials can be used for the expandable member in accordance with the disclosed subject matter. For example, the expandable member can be made from polymeric material, including compliant, semi-compliant, or non-compliant polymeric material or polymeric blends.

In one embodiment, the polymeric material is a polyamide/polyether block copolymer (commonly referred to as PEBA or polyether-block-amide). The polyamide and polyether segments of the block copolymers can be linked through amide or ester linkages. The polyamide block can be selected from various aliphatic or aromatic polyamides known in the art. Some non-limiting examples of an aliphatic include nylon 12, nylon 11, nylon 9, nylon 6, nylon 6/12, nylon 6/11, nylon 6/9, and nylon 6/6. In one embodiment, the polyamide is nylon 12. The polyether block can be selected from various polyethers known in the art. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material can also be utilized such as for example, PEBAX® materials supplied by Arkema (France). Additionally balloon grillamid can be used as the material for the expandable member. Various techniques for forming a balloon from polyamide/polyether block copolymer are known in the art. One such example is disclosed in U.S. Pat. No. 6,406,457 to Wang, the disclosure of which is incorporated by reference in its entirety.

In another embodiment, the expandable member is formed from polyamides. The polyamide can have substantial tensile strength, is resistant to pin-holing even after folding and unfolding, and is generally scratch resistant, such as those disclosed in U.S. Pat. No. 6,500,148 to Pinchuk, the disclosure of which is incorporated herein by reference in its entirety. Some non-limiting examples of polyamide materials suitable for the balloon include nylon 12, nylon 11, nylon 9, nylon 69 and nylon 66. Other suitable materials for constructing non-compliant balloons are polyesters such as polyethylene terephthalate) (PET), Hytrel thermoplastic polyester, and poly(ethylene.

In another embodiment, the balloon is formed of a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. TECOTHANE® grade 1065D can be used and has a Shore durometer of 65D, an elongation at break of about 300%, and a high tensile strength at yield of about 10,000 psi. However, other suitable grades can be used, including TECOTHANE® 1075D, having a Shore D hardness of 75. Other suitable compliant polymeric materials include ENGAGE® (DuPont Dow Elastomers (an ethylene alpha-olefin polymer)) and EXACT® (Exxon Chemical), both of which are thermoplastic polymers. Other suitable compliant materials include, but are not limited to, elastomeric silicones, latexes, and urethanes.

The compliant material can be cross linked or uncrosslinked, depending upon the balloon material and characteristics required for a particular application. The polyurethane balloon materials are not crosslinked. However, other suitable materials, such as the polyolefinic polymers ENGAGE® and EXACT®, can be crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid over expanding the balloon to an undesirably large diameter.

In another embodiment, the balloon is formed from a low tensile set polymer such as a silicone-polyurethane copolymer. The silicone-polyurethane can be an ether urethane and more specifically an aliphatic ether urethane such as PURSIL AL 575A and PURSIL AL10, (Polymer Technology Group), and ELAST-EON 3-70A (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as, but not limited to, an isoprene such as an AB and ABA polystyrene-block-isoprene), a neoprene, an AB and ABA polystyrene-block-butadiene) such as styrene butadiene styrene (SBS) and styrene butadiene rubber (SBR), and 1,4-polybutadiene. In one embodiment, the diene polymer is an isoprene including isoprene copolymers and isoprene block copolymers such as poly(styrene-block-isoprene).

In one embodiment, the isoprene is a styrene-isoprene-styrene block copolymer, such as Kraton 1161K available from Kraton, Inc. However, a variety of suitable isoprenes can be used including HT 200 available from Apex Medical, Kraton R 310 available from Kraton, and isoprene (i.e., 2-methyl-1,3-butadiene) available from Dupont Elastomers. Neoprene grades useful in the disclosed subject matter include HT 501 available from Apex Medical, and neoprene (i.e., polychloroprene) available from Dupont Elastomers, including Neoprene G, W, T and A types available from Dupont Elastomers. Examples of other balloon and catheter embodiments which can be employed in accordance with the disclosed subject matter include U.S. Pat. Nos. 4,748,982; 5,496,346; 5,626,600; 5,300,085; and 6,406,457 and application Ser. Nos. 12/371,426; 11/539,944; and 12/371,422, each of which is hereby incorporated by reference in its entirety.

In accordance with another aspect of the disclosed subject matter, the expandable member is a balloon having a multi-layer construction. The multilayer construction can include at least a first layer and a second layer having a combined wall thickness. As embodied herein, for purpose of illustration and not limitation, the first layer is made of a first polymer material having a first maximum blow-up-ratio, and the second layer is made of a second polymer material having a second maximum blow-up-ratio greater than the first maximum blow-up-ratio. The at least first and second layers define a compliance less than that of a single layer made of the first polymer material with a wall thickness equal to the combined wall thickness.

A multilayered balloon of the disclosed subject matter can be formed in whole or in part of coextruded polymeric tubular layers, and provides for ease of manufacture of the balloon and balloon catheter formed therefrom. The multilayered balloon is typically formed by conventional blow-molding in which a multilayered polymeric tube is radially expanded within a balloon mold. The resulting multilayered balloon has an inflated shape which corresponds to the inner surface of the mold and which has a diameter about equal to the inner diameter of the balloon mold, commonly referred to as the balloon's nominal working diameter. The nominal pressure is the inflation pressure required to fill the balloon to the nominal working diameter. In accordance with the disclosed subject matter, the balloon expands a very small amount (i.e., noncompliantly) at pressures above the nominal pressure. As a result, the balloon minimizes injury to a patient's blood vessel, which can otherwise occur if the balloon continues to expand a substantial uncontrolled amount at increasing inflation pressures above nominal.

The blow-up-ratio (BUR) of the balloon formed from a polymer tube should be understood to refer to the ratio of the outer diameter of the blown balloon expanded within the mold (i.e., the mold inner diameter) to the inner diameter of the polymer tube prior to being expanded in the mold. Each individual layer of the multilayered balloon similarly has its own BUR based on the ratio of the inner diameter of the mold and the inner diameter (prior to expansion in the mold) of the layer of the polymeric tube. For a given balloon wall thickness, the rupture strength generally increases and the radial compliance decreases as the balloon BUR increases. For standard pressure driven blow molding of catheter balloons, typical BURs range from about 4.5 to about 8.0 depending on the material and the product application.

A multilayer balloon in accordance with the disclosed subject matter increases the amount of balloon material that is highly oriented in the radial direction, to provide a balloon with limited radial expansion at increasing inflation pressures (i.e., to provide a noncompliant balloon). Specifically, a multilayered balloon of the disclosed subject matter has polymeric materials that can be expanded to higher BURs as the inner layer(s) of the balloon, while lower BUR materials are the outer layer(s) of the balloon. In one embodiment, the balloon has a first layer of a first polymeric material and a second layer of a second polymeric material which has a lower Shore durometer hardness than the first polymeric material and which can be expanded during balloon blowing to a higher BUR (without rupturing or tearing) than the higher Shore durometer hardness material of the first layer, and the second layer is an inner layer relative to the first layer. For example, in one embodiment, the multilayered balloon inner layer is formed of a polyether block amide (PEBA) material (e.g., commercially available as PEBAX®) having a Shore durometer hardness of about 60-70D while the outer layer is formed of a PEBA material having a higher Shore durometer hardness of about 70-72D. However, a variety of suitable materials can be used including materials which are of the same material classification/family, or different classes of materials. The multilayered balloon generally has two or more layers (i.e., layers formed of materials which differ in some respect such as different Shore durometer hardnesses), although it typically does not have more than five layers.

Despite presence of the lower durometer material forming the second (inner) layer of the multilayered balloon, a multilayer balloon of the disclosed subject matter provides a balloon which has a very low compliance. For example, a balloon of the disclosed subject matter having a first (outer) layer of a first durometer, and one or more inner layer(s) of successively lower durometers (i.e., increasingly softer materials), has a lower compliance than a balloon having about the same wall thickness but formed of 100% of the highest durometer material (i.e., the material forming the outer-most layer of the balloon of the disclosed subject matter). Compared to a balloon formed of 100% of the highest durometer material, a balloon of the disclosed subject matter has effectively replaced a part of the balloon wall thickness with the layer(s) of lower durometer (softer) material(s), which would typically be expected to increase the compliance. While not wishing to be bound by theory, it is believed that the balloon provides the noncompliant behavior through the specific combination of highly oriented layers of the balloon, and particularly by maximizing the orientation of the inner layer(s) of the balloon. The inner layer orientation significantly affects compliance of the balloon. By selecting and arranging different materials that can be blown to different BURs in accordance with the disclosed subject matter, the balloon has layers with successively increasing BURs from the outer to the inner layer(s), such that the BUR of each layer can be maximized and the inner layer(s) have particularly high BURs. The layers of the balloon are therefore optimized for compliance purposes. Although additional layers may be added to the balloon, to, for example, increase the total wall thickness to a desired value, the arrangement of the basic layers in accordance with the disclosed subject matter cannot be varied without resulting in a higher compliance balloon.

Additionally, the disclosed subject matter can alternatively provide for a multilayer balloon with a low compliance but with very thin walls. For example, one embodiment is directed to a multilayered balloon having a first (outer) layer of a first durometer material and one or more inner layer(s) of successively lower durometer materials which has a compliance not substantially greater than (e.g., not more than about 10% to about 20% greater than), and approximately about equal to a balloon which is formed of 100% of the highest durometer material but which has a larger wall thickness than the multilayered balloon of the disclosed subject matter. The embodiment of the balloon having a very thin total wall thickness provides an improved low profile and flexibility due to the thinner walls of the balloon, but, in accordance with the disclosed subject matter, nonetheless continues to provide a low compliance despite the thin wall.

The rupture pressure and compliance of a balloon are affected by the strength (e.g., hoop strength) of a balloon. Because a softer material generally has a relatively lower hoop strength, the presence of the lower durometer material forming the inner layer(s) of the balloon is not generally expected to provide a relatively higher modulus balloon. However, a multilayered balloon of the disclosed subject matter can have a higher modulus than, and a rupture pressure which is not substantially less than, a balloon formed of 100% of the highest durometer material.

The presence of the lower durometer material inner layer(s) does provide layers of increased softness, and therefore can provide a balloon that is softer and more flexible than a balloon formed of 100% of the highest durometer material.

A balloon of the disclosed subject matter can arrange layers so that the highest durometer material has on an inner surface thereof a layer of a lower durometer material, and configures the layers to provide for a maximized BUR which produces an improved combination of characteristics including a very low compliance. However, with the inner layer(s) of the balloon of the disclosed subject matter optimized for compliance purposes as discussed above, one embodiment of a balloon of the disclosed subject matter has an outer-most layer of a relatively soft material, to, for example, enhance stent retention, it desired.

The compliance of the balloon should be understood to refer to the degree to which the polymeric wall of the balloon stretches/distends as the balloon expands beyond the nominal diameter of the balloon. The compliance curve expresses the balloon outer diameter as a function of increasing inflation pressure in millimeters/atmospheres (mm/atm), so that a steeper curve or section of the curve indicates a higher compliance than a flatter curve. The term "noncompliant", should be understood to mean a balloon with compliance of not greater than about 0.03 mm/atm, and in one embodiment not greater than about 0.025 mm/atm. In contrast, compliant balloons typically have a compliance of greater than about 0.045 mm/atm. A noncompliant balloon of the disclosed subject matter generally has a compliance above nominal of about 0.01 to about 0.02 mm/atm, for a 3.0 mm diameter balloon. The compliance of the balloon is typically about 25% to about 50% less than the compliance of a balloon with a similar wall thickness but made from 100% of the first (e.g., highest durometer) material.

In one embodiment, the polymeric material of the first layer and the polymeric material of the second layer of the multilayered balloon are elastomers, which typically have a lower flexural modulus than nonelastomers. Elastomeric polymers suitable for forming the first and/or second layer of the multilayered balloon typically have a flexural modulus of about 40 kpsi to about 110 kpsi. Thus, unlike nonelastomeric materials such as PET, the multilayered noncompliant balloon of the disclosed subject matter can be formed of one or more elastomers which provide for improved balloon flexibility.

Balloon in accordance with the disclosed subject matter can be formed by any suitable method. For example, one method generally comprises selecting a first and a second polymeric material, the second polymeric material having been determined to have a higher maximum attainable BUR than the first polymeric material, and forming a multilayered tube having a first layer of the first polymeric material, and a second layer of the second polymeric material wherein the second layer is an inner layer relative to the first layer. The maximum attainable BUR of a polymeric material is typically determined experimentally, although characteristics such as the ultimate tensile strength and elongation to break of the material maybe indicative at least for some materials (e.g., a material having a relatively higher ultimate tensile strength and elongation to break is expected, in general, to have a higher maximum BUR). The inner diameter of each layer of the multilayered tube is selected so that the ratio of the inner diameter of the balloon mold and the inner diameter of the layer of the multilayered tube (prior to being radially expanded in the balloon mold) is substantially at a maximum blow-up-ratio for the polymeric material forming the layer. Thus, the method includes forming the blow-molded multilayered balloon by radially expanding the multilayered tube in a mold, so that radially expanding the tube to the mold inner diameter radially expands each layer substantially to the maximum blow-up-ratio of the polymeric material forming the layer, such that the multilayered balloon has a lower compliance above the nominal working diameter than a balloon consisting of the first elastomeric polymeric material.

The multilayered balloon of the disclosed subject matter provides a very low compliance for controlled balloon expansion, without compromising relatively high flexibility and softness for excellent ability to track the patient's vasculature and cross lesions. As a result, the adjustable balloon catheter of the disclosed subject matter has improved performance due to the flexibility, softness, and controlled expansion of the balloon. The balloon provides the surprising result of a very low compliance from the addition of the lower durometer (softer) second material. Consequently, a multilayered balloon of the disclosed subject matter will provide a much lower compliance than a balloon with the same wall thickness but made from just the higher durometer (stiffer) material, or will provide a much thinner walled balloon but without the expected increase in compliance.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Many modifications, variations, or other equivalents to the specific embodiments described above will be apparent to those familiar with the art. It is intended that the scope of this disclosed subject matter be defined by the claims below and those modifications, variations and equivalents apparent to practitioners familiar with this art Thus, it is intended that the disclosed subject matter include modifications and variations that are within the scope of the appended claims and their equivalents.

The invention claimed is:

1. An adjustable balloon catheter comprising:
   an inner tubular member having a proximal end portion, a distal end portion, and a length therebetween, the inner tubular member further having an inflation lumen defined therein;
   an expandable member coupled to the distal end portion of the inner tubular member and having an inner chamber in fluid communication with the inflation lumen, the expandable member transitionable between a deflated configuration and an inflated configuration, the expandable member defining a longitudinal axis and having a non-cylindrical shape along at least a portion of a working length thereof when in the inflated configuration;
   an outer tubular member movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member.

2. The adjustable balloon catheter according to claim 1, further comprising a flushing lumen defined between the inner tubular member and the outer tubular member, wherein the distal end of the outer tubular member has at least one flushing port defined therethrough in fluid communication with the flushing lumen.

3. The adjustable balloon catheter according to claim 2, further comprising an adaptor in fluid communication with the flushing lumen to receive a supply of contrast fluid.

4. The adjustable balloon catheter according to claim 1, wherein the non-cylindrical shape of the expandable member includes a distal end section having a first diameter and a proximal end section having a second diameter when in the inflated configuration, the first diameter being different than the second diameter.

5. The adjustable balloon catheter according to claim 1, wherein the non-cylindrical shape of the expandable member includes a frustro-conical shape along the longitudinal axis in the inflated configuration.

6. The adjustable balloon catheter according to claim 1, wherein the non-cylindrical shape of the expandable member includes a spiral shape along the longitudinal axis in the inflated configuration.

7. The adjustable balloon catheter according to claim 6, wherein the spiral shape extends radially from the longitudinal axis a varied distance along the working length in the inflated configuration.

8. The adjustable balloon catheter according to claim 6, wherein an exterior surface of the expandable member in the inflated configuration defines a spiral flow path along the longitudinal axis.

9. The adjustable balloon catheter according to claim 1, wherein the expandable member includes a helical shape along the longitudinal axis in the inflated configuration.

10. The adjustable balloon catheter according to claim 9, wherein the helical shape extends radially from the longitudinal axis a substantially constant distance along the working length in the inflated configuration.

11. The adjustable balloon catheter according to claim 9, wherein an exterior surface of the expandable member in the inflated configuration defines a helical flow path along the longitudinal axis.

12. The adjustable balloon catheter according to claim 1, wherein an exterior surface of the expandable member defines a longitudinal flow path along the longitudinal axis.

13. The adjustable balloon catheter according to claim 1, wherein an exterior surface of the expandable member defines at least one isolated chamber along the longitudinal axis in the inflated configuration.

14. The adjustable balloon catheter according to claim 13, wherein the at least one isolated chamber includes a plurality of isolated chambers spaced apart along the working length.

15. The adjustable balloon catheter according to claim 1, wherein the expandable member further includes a cylindrical shape along another portion of the working length in the inflated configuration.

16. The adjustable balloon catheter according to claim 1, wherein the working length of the expandable member includes a plurality of cylindrical shaped segments spaced along the longitudinal axis.

17. The adjustable balloon catheter according to claim 1, wherein the expandable member has an outer diameter dependent upon the exposed length.

18. The adjustable balloon catheter according to claim 1, wherein the expandable member includes a proximal portion proximal to the working length, the proximal portion remaining with the outer tubular member when positioned in the retracted position.

19. The adjustable balloon catheter according to claim 18, wherein the expandable member has a folded arrangement in the deflated configuration, the proximal portion remaining at least partially folded within the outer tubular member in the inflated configuration.

20. The adjustable balloon catheter according to claim 1, further comprising a reinforced proximal sleeve at a proximal end portion of the expandable member.

21. The adjustable balloon catheter according to claim 1, wherein the expandable member includes a semicompliant material.

22. The adjustable balloon catheter according to claim 1, wherein the expandable member includes compliant material.

23. The adjustable balloon catheter according to claim 1, wherein the expandable member includes a multilayer construction.

24. The adjustable balloon catheter according to claim 23, wherein the expandable member includes at least a first layer and a second layer having a combined wall thickness, wherein the first layer made of a first polymer material having a first maximum blow-up-ratio and the second layer made of a second polymer material having a second maximum blow-up-ratio greater than the first maximum blow-up-ratio, wherein the at least first and second layers define a compliance less than that of a single layer made of the first polymer material with a wall thickness equal to the combined wall thickness.

25. An adjustable balloon catheter comprising:
    an inner tubular member having a proximal end portion, a distal end portion, and a length therebetween, the inner tubular member further having an inflation lumen defined therein;
    an expandable member coupled to the distal end portion of the inner tubular member and having an inner chamber in fluid communication with the inflation lumen, the expandable member transitionable between a deflated configuration and an inflated configuration, the expandable member defining a longitudinal axis and having a working length in the inflated configuration; and
    an outer tubular member movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member,
    wherein the inner tubular member extends at least partially through the expandable member, the inner tubular member having a plurality of inflation ports defined therein along the working length for fluid communication between the inflation lumen and the inner chamber.

26. A method of deploying a medical device, comprising:
    providing an adjustable balloon catheter including
        an inner tubular member having a proximal end portion, a distal end portion, and a length therebetween, the inner tubular member further having an inflation lumen defined therein,
        an expandable member coupled to the distal end portion of the inner tubular member and having an inner chamber in fluid communication with the inflation lumen, the expandable member transitionable between a deflated configuration and an inflated configuration, the expandable member defining a longitudinal axis and having a non-cylindrical shape along at least a portion of a working length thereof when in the inflated configuration, and
        an outer tubular member movable relative to the inner tubular member, the outer tubular member including a distal end, the outer tubular member being moveable between an extended position disposed over the expandable member and a retracted position proximal to the extended position, the outer tubular member being selectively positioned between the extended position and the retracted position to define an exposed length of the working length of the expandable member;
    retracting the outer tubular member in a proximal direction to define the exposed length of the working length of the expandable member;
    inflating the exposed length of the expandable member to the inflated configuration; and
    deflating the expandable member to the deflated configuration.

27. The method according to claim 26, wherein inflating the exposed length includes
    inserting the catheter into a body lumen of a patient;
    introducing fluid into the inflation lumen; and
    withdrawing the catheter from the body lumen of a patient.

28. The method according to claim 26, wherein retracting the outer tubular member includes selecting the exposed length of the expandable member, the expandable member having an outer diameter selectively determined by the outer tubular member.

* * * * *